(12) United States Patent
Ikeda et al.

(10) Patent No.: US 10,317,399 B2
(45) Date of Patent: Jun. 11, 2019

(54) SAMPLE ANALYZER

(71) Applicant: Toshiba Medical Systems Corporation, Otawara-shi (JP)

(72) Inventors: Naru Ikeda, Tokyo (JP); Motoji Haragashira, Utsunomiya (JP); Shoichi Kanayama, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 148 days.

(21) Appl. No.: 15/293,806

(22) Filed: Oct. 14, 2016

(65) Prior Publication Data

US 2017/0108495 A1 Apr. 20, 2017

(30) Foreign Application Priority Data

Oct. 15, 2015 (JP) .................................. 2015-206591

(51) Int. Cl.
*G01N 33/543* (2006.01)
*G01R 33/12* (2006.01)

(52) U.S. Cl.
CPC . *G01N 33/54333* (2013.01); *G01N 33/54326* (2013.01); *G01N 33/54366* (2013.01); *G01R 33/1269* (2013.01); *G01R 33/1276* (2013.01)

(58) Field of Classification Search
CPC ......... G01N 33/5433; G01N 33/54326; G01N 33/54366; G01R 33/1269; G01R 33/1276
See application file for complete search history.

(56) References Cited

U.S. PATENT DOCUMENTS

| 7,776,221 | B2 | 8/2010 | Brassard | |
|---|---|---|---|---|
| 2011/0050215 | A1* | 3/2011 | Kahlmann | G01N 27/745 |
| | | | | 324/244 |
| 2014/0014856 | A1* | 1/2014 | Cox | G01N 21/6428 |
| | | | | 250/459.1 |

FOREIGN PATENT DOCUMENTS

| JP | 2007-221955 | 8/2007 |
|---|---|---|
| JP | 2012-215553 | 11/2012 |
| WO | WO 2008/072149 A2 | 6/2008 |

(Continued)

OTHER PUBLICATIONS

"Minicare I-20 Enabling near patient blood testing in the acute care setting", Philips Healthcare, Magnotech technologies, http://www.philips.co.uk/healthcare/product/HCNOCTN496/minicare-I-20, 2016, 9 pages.

(Continued)

*Primary Examiner* — Benjamin R Whatley
(74) *Attorney, Agent, or Firm* — Oblon, McClelland, Maier & Neustadt, L.L.P.

(57) ABSTRACT

According to one embodiment, a sample analyzer includes a detector, a first generator and a second generator. The detector detects a target substance bonded to a magnetic particle collected to a sensing area in the cartridge. The first generator applies a magnetic field for releasing the magnetic particles from the sensing area. The second generator includes a permanent magnet configured to generate a magnetic field for attracting the magnetic particles to the sensing area, a first soft magnetic material, and a second magnetic material. The second generator switches application and shut-off of a magnetic field by moving the permanent magnet relative to the first soft magnetic material and the second soft magnetic material.

18 Claims, 25 Drawing Sheets

(56) References Cited

FOREIGN PATENT DOCUMENTS

WO     WO 2008/072156 A2     6/2008

OTHER PUBLICATIONS

Richard Luxton, et al. "Use of External Magnetic Fields to Reduce Reaction Times in an Immunoassay Using Micrometer-Sized Paramagnetic Particles as Labels (Magnetoimmunoassay)", Analytical Chemistry, vol. 76, No. 6, 2004, 5 pages.

* cited by examiner

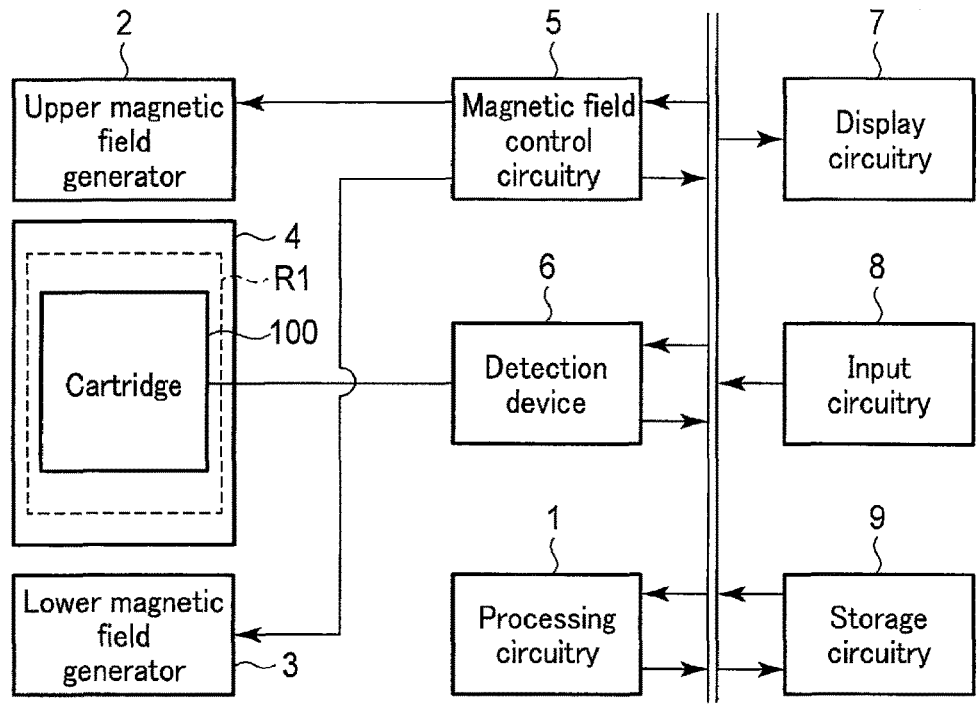
F I G. 1
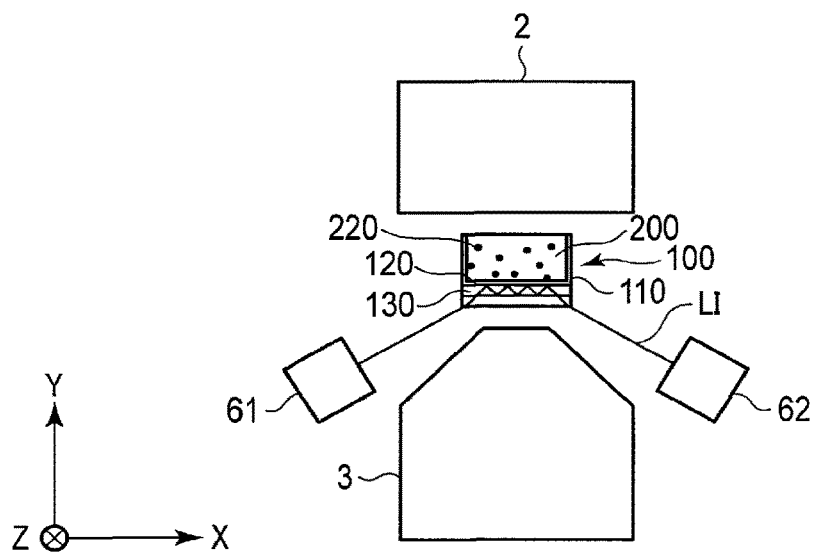
F I G. 2

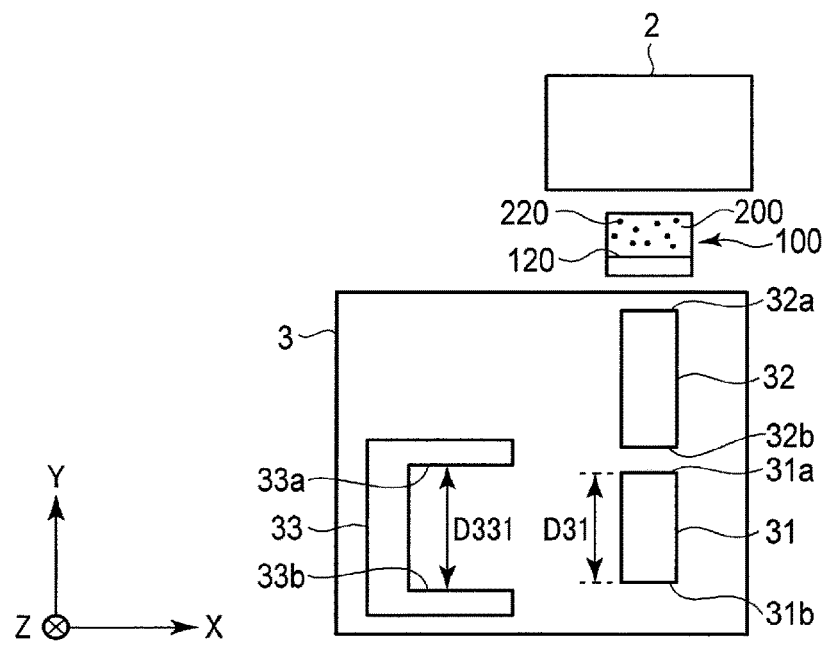
F I G. 3
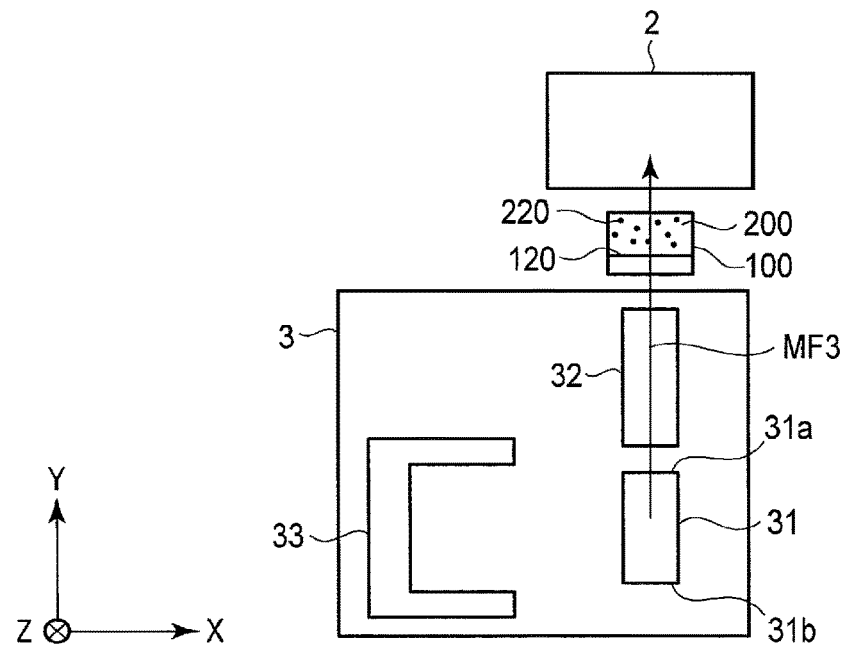
F I G. 4A

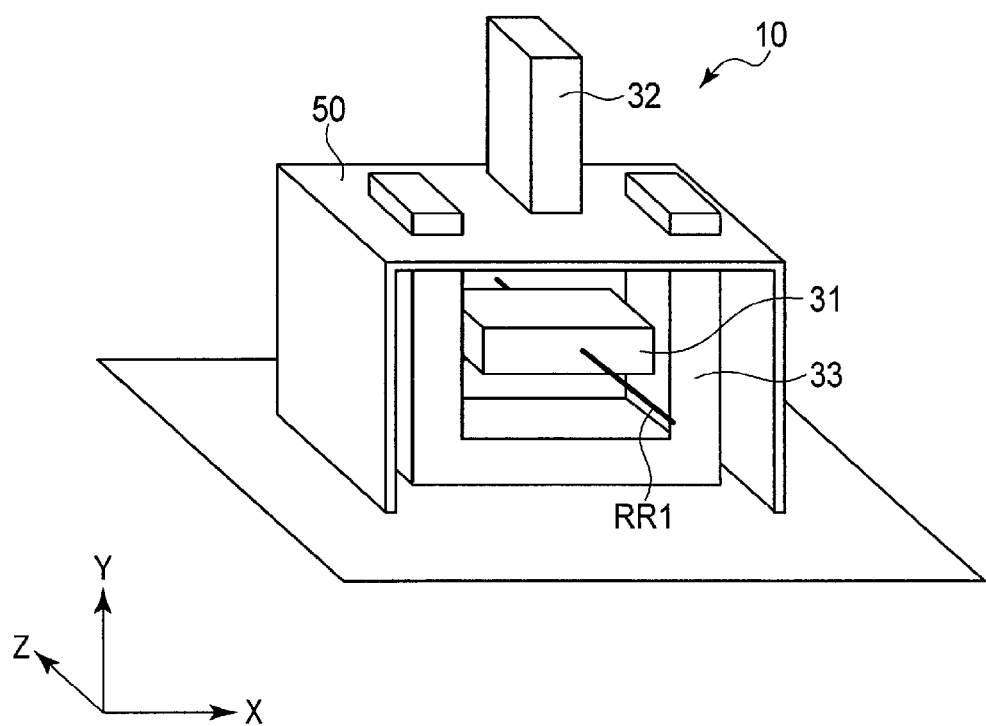
F I G. 5E

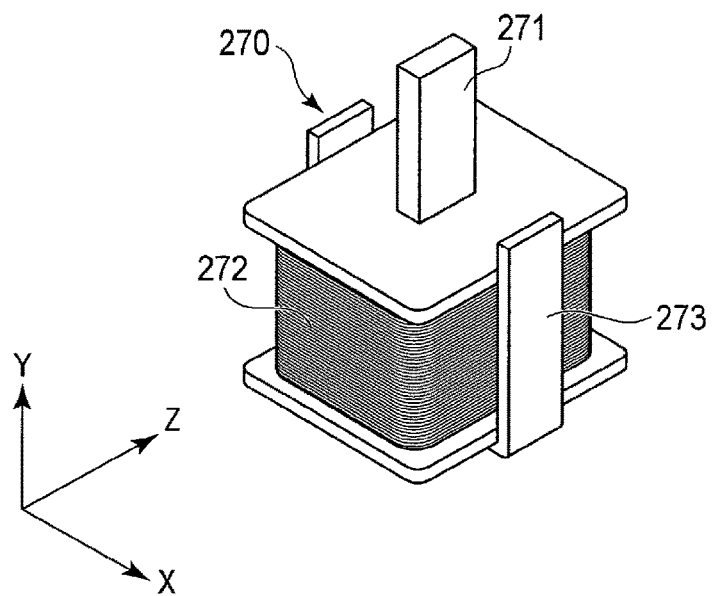
F I G. 6A
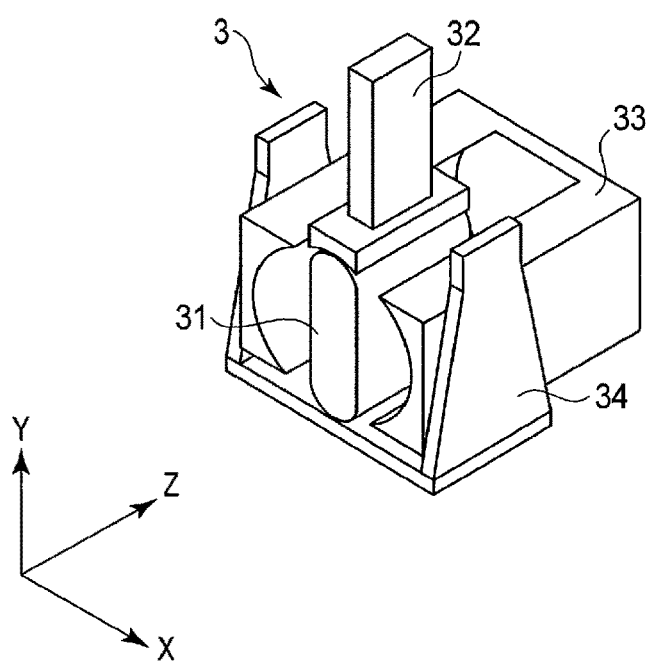
F I G. 6B

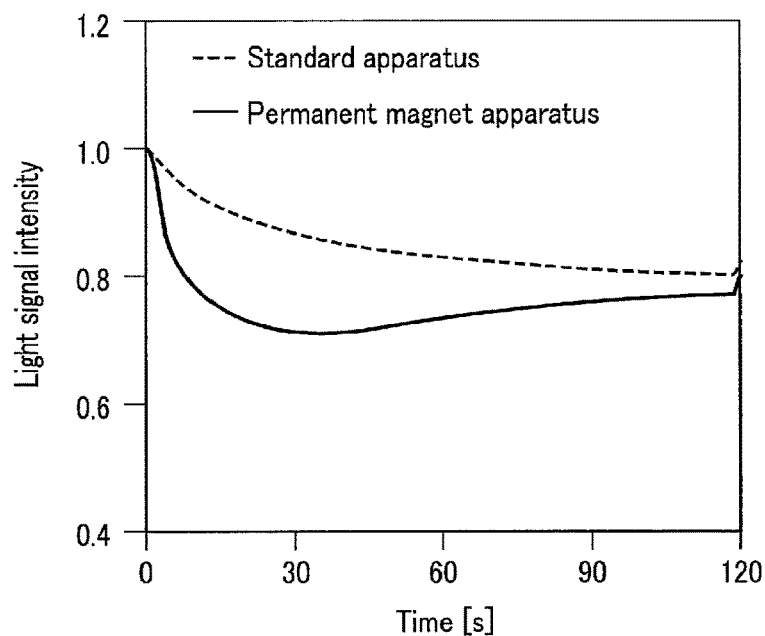
F I G. 7
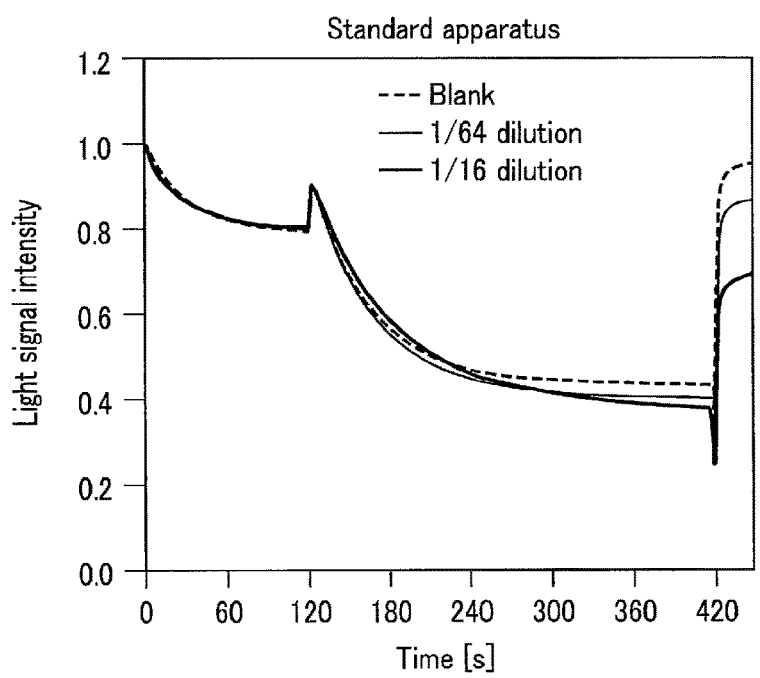
F I G. 8

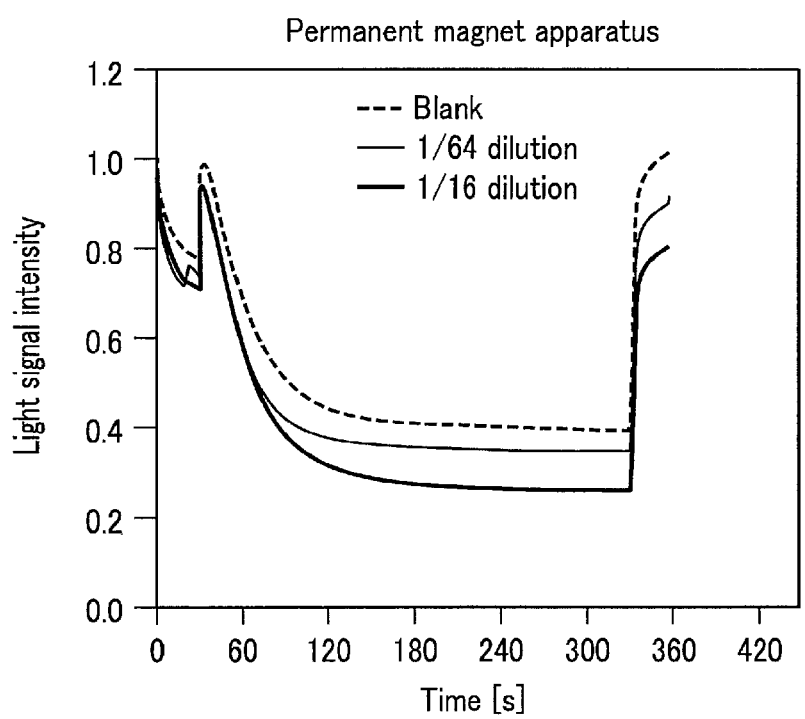
F I G. 9

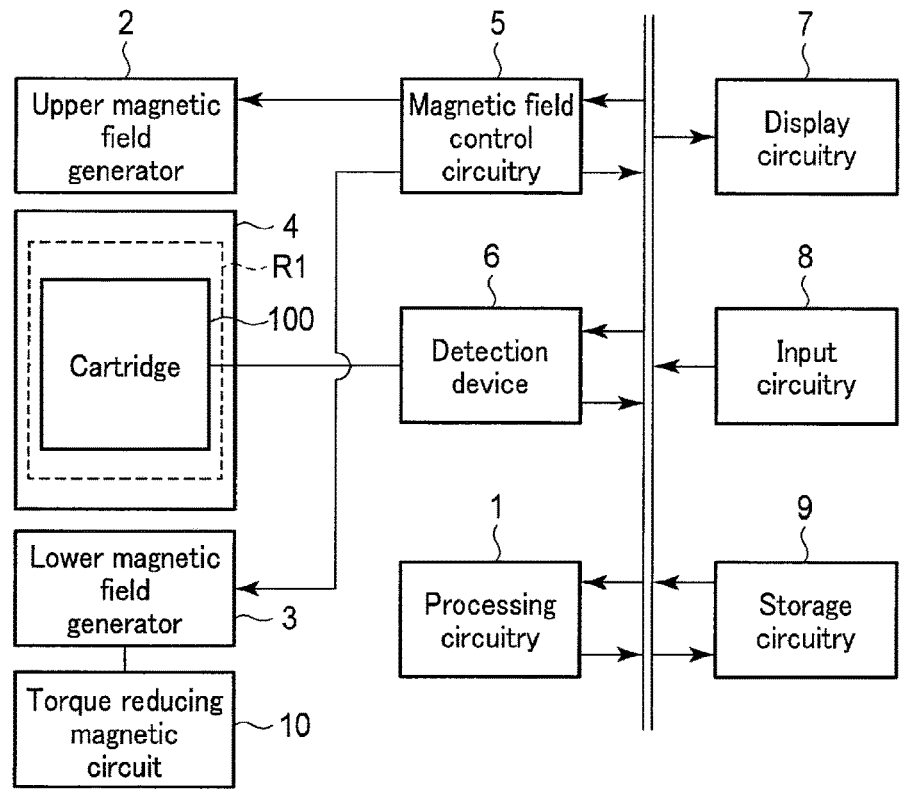
F I G. 10
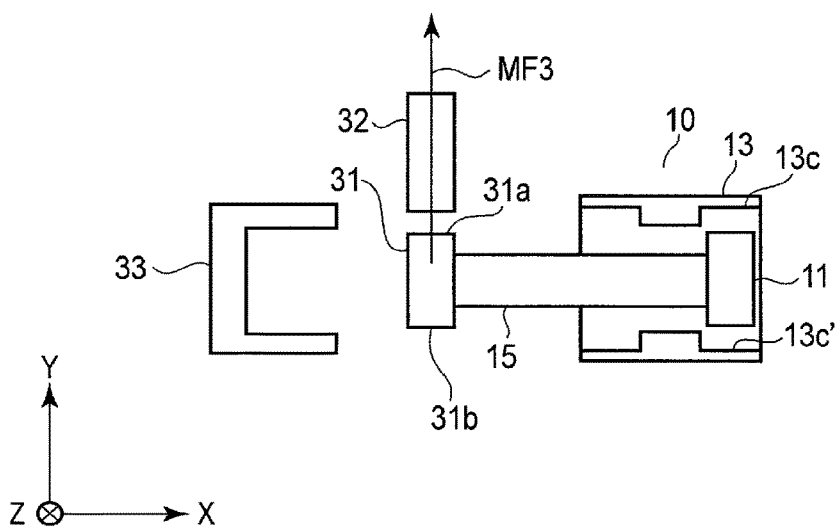
F I G. 11A

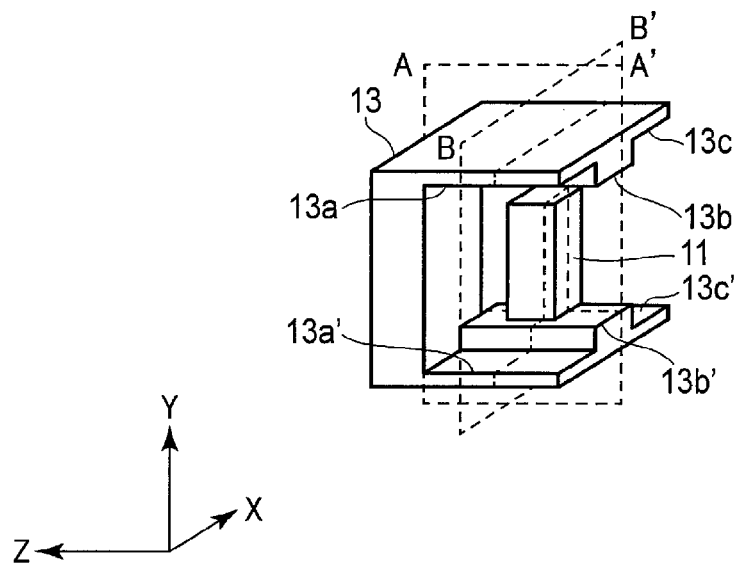
F I G. 12A
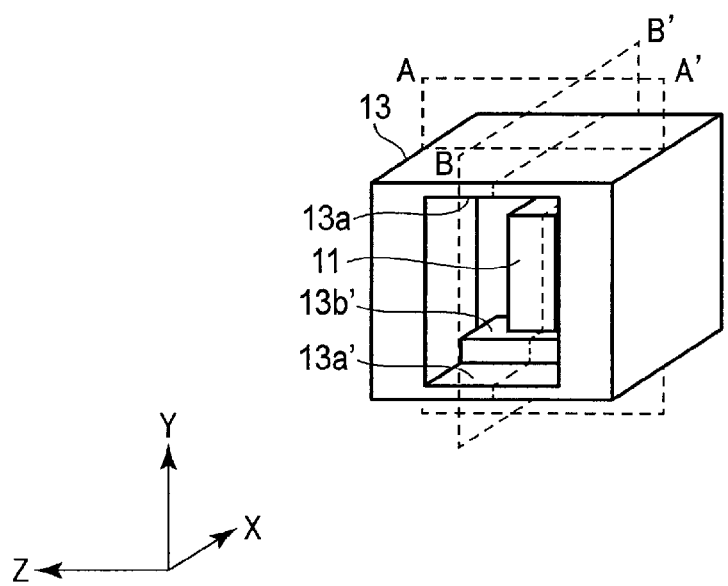
F I G. 12B

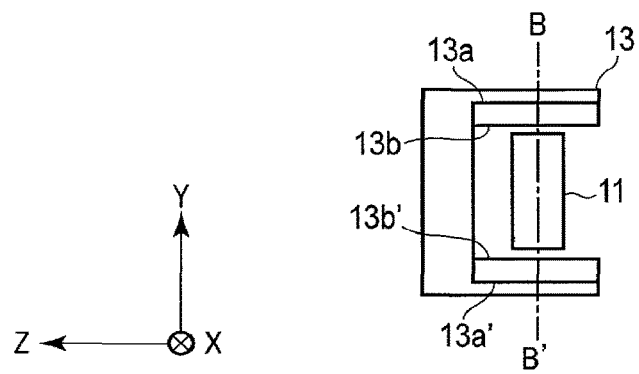
F I G. 12C
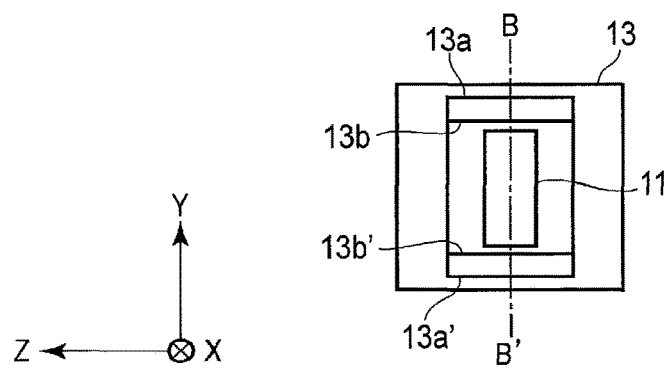
F I G. 12D
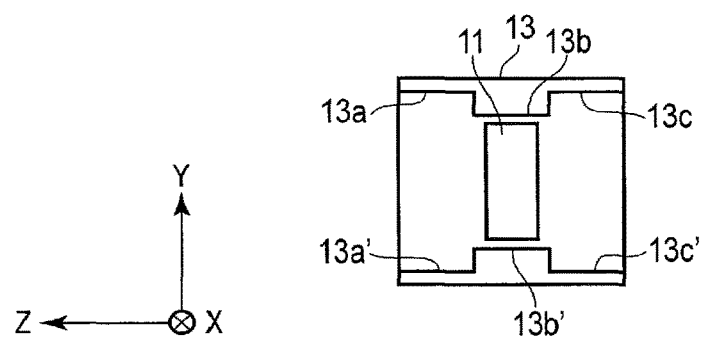
F I G. 12E

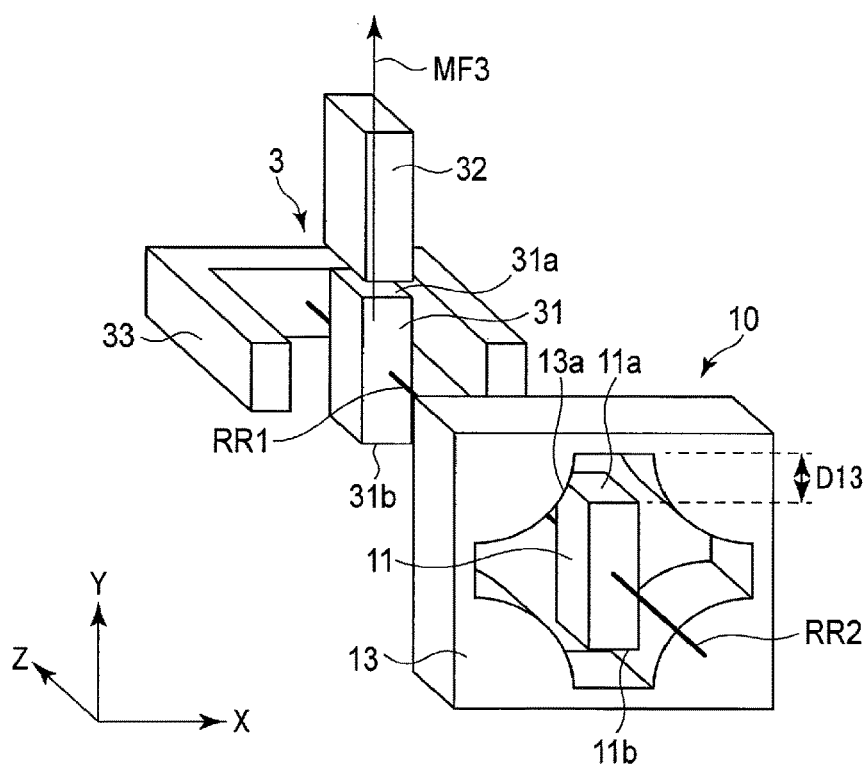
F I G. 13A
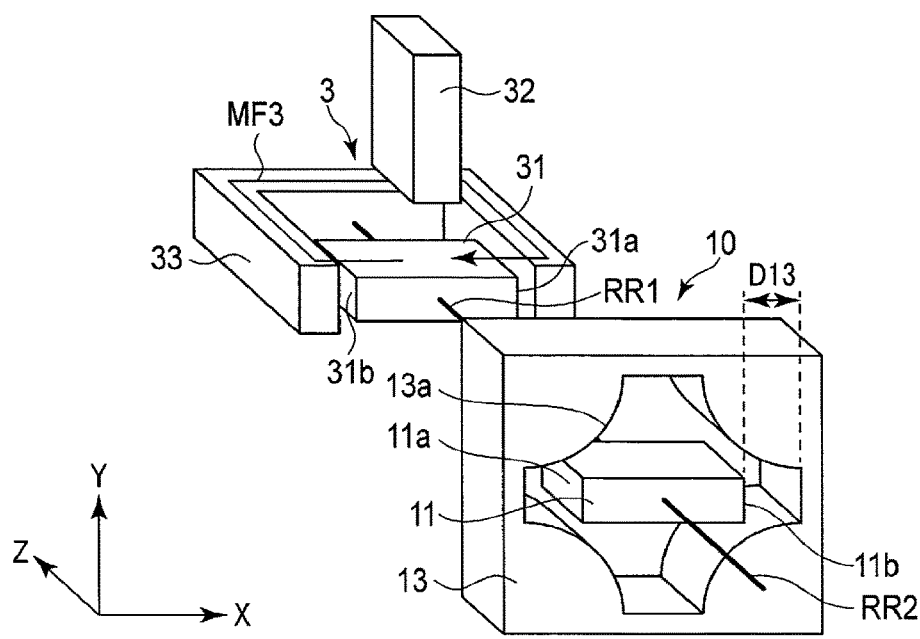
F I G. 13B

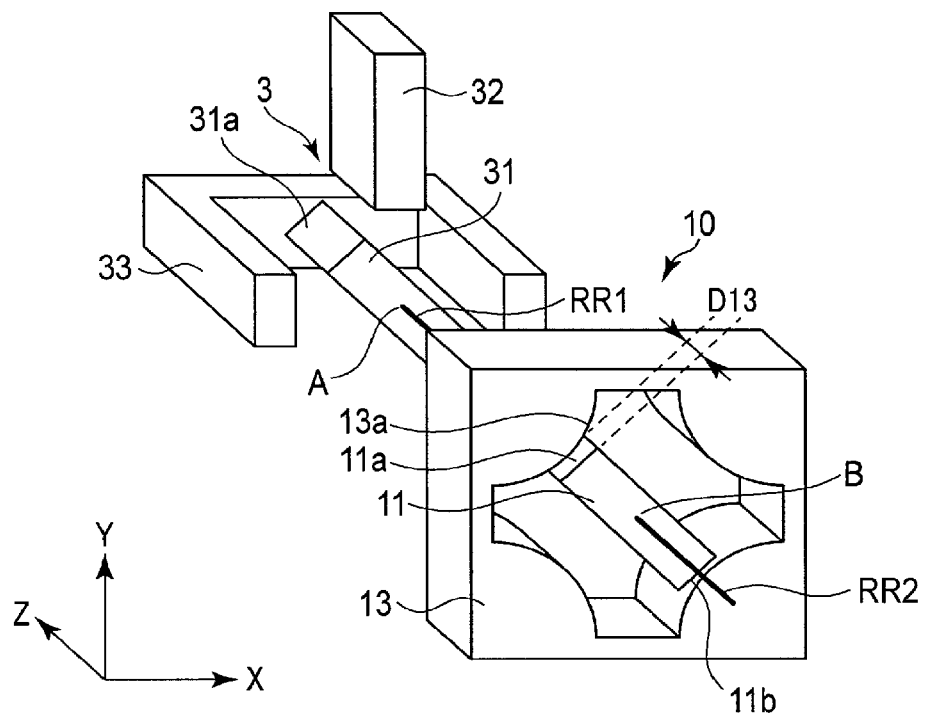
F I G. 13C
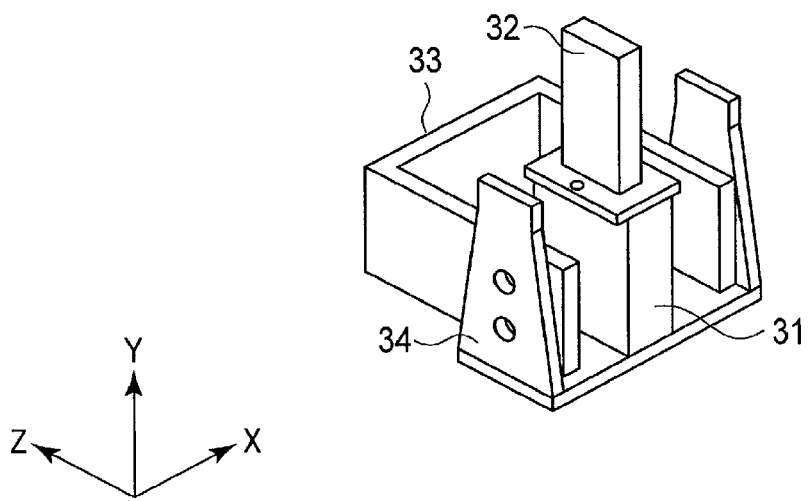
F I G. 14A

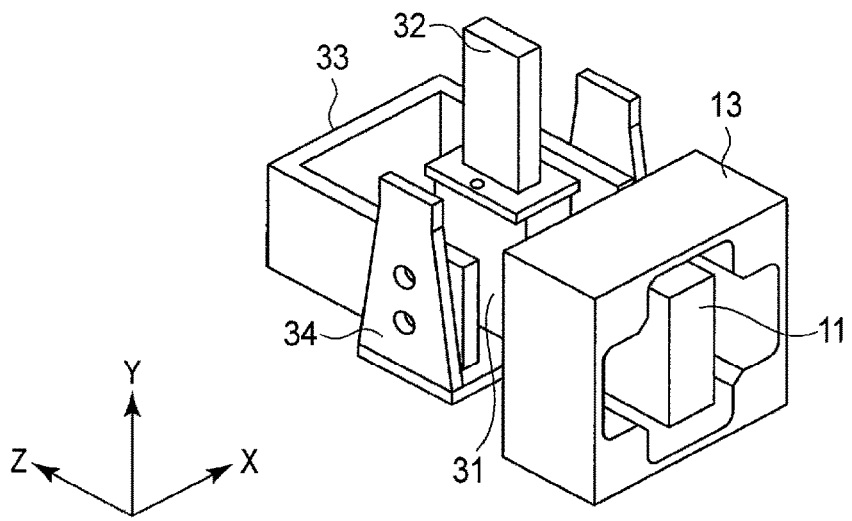
F I G. 14B
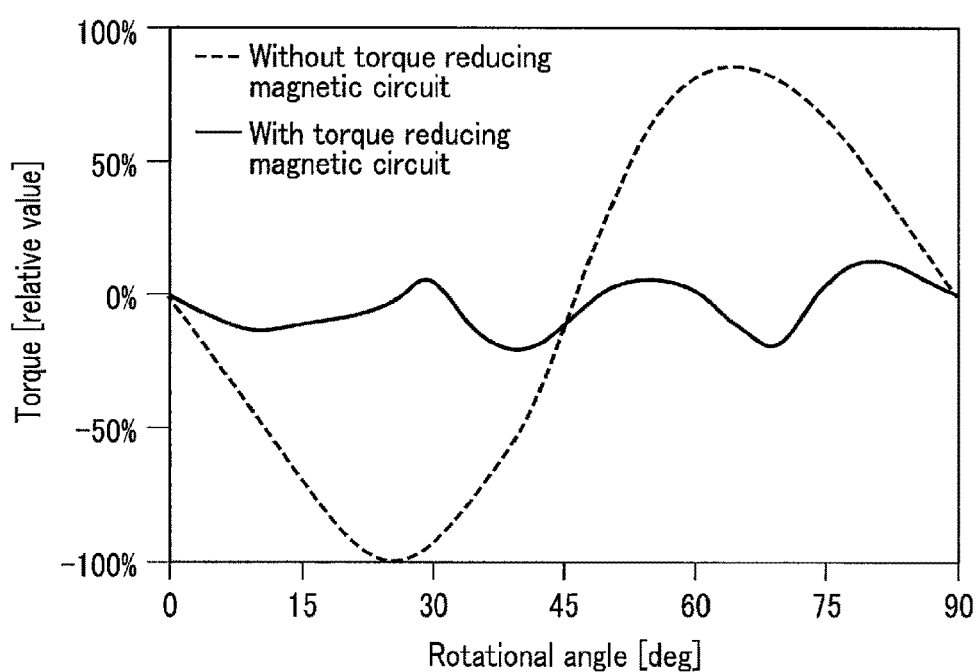
F I G. 15

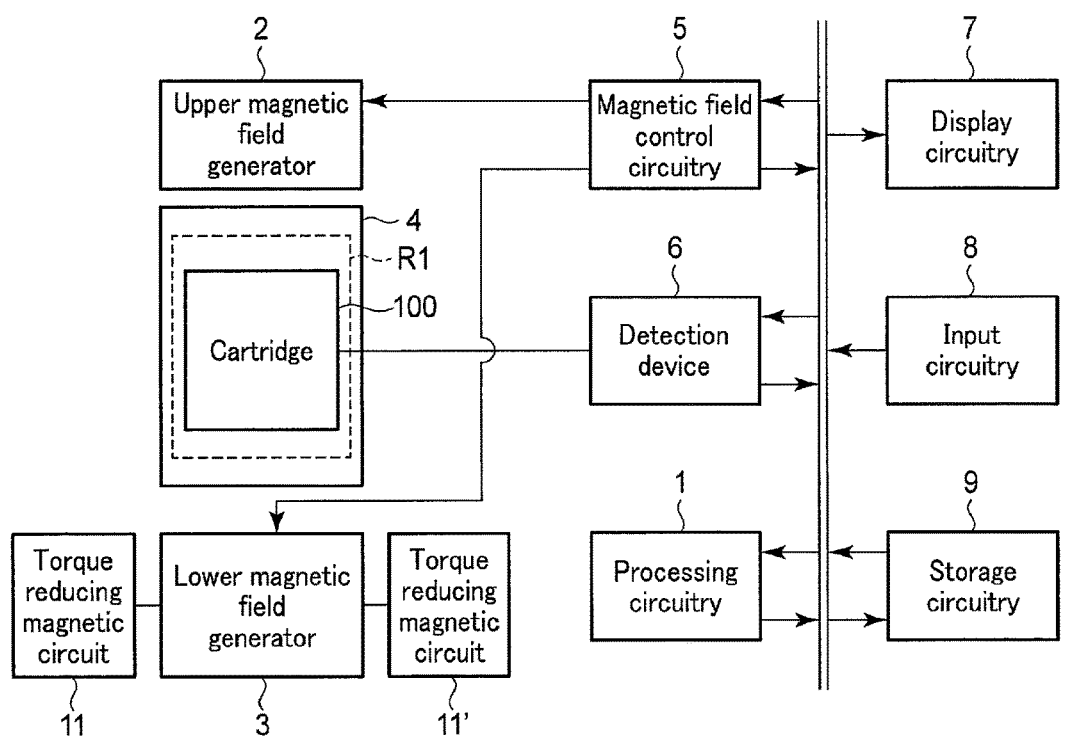
F I G. 16

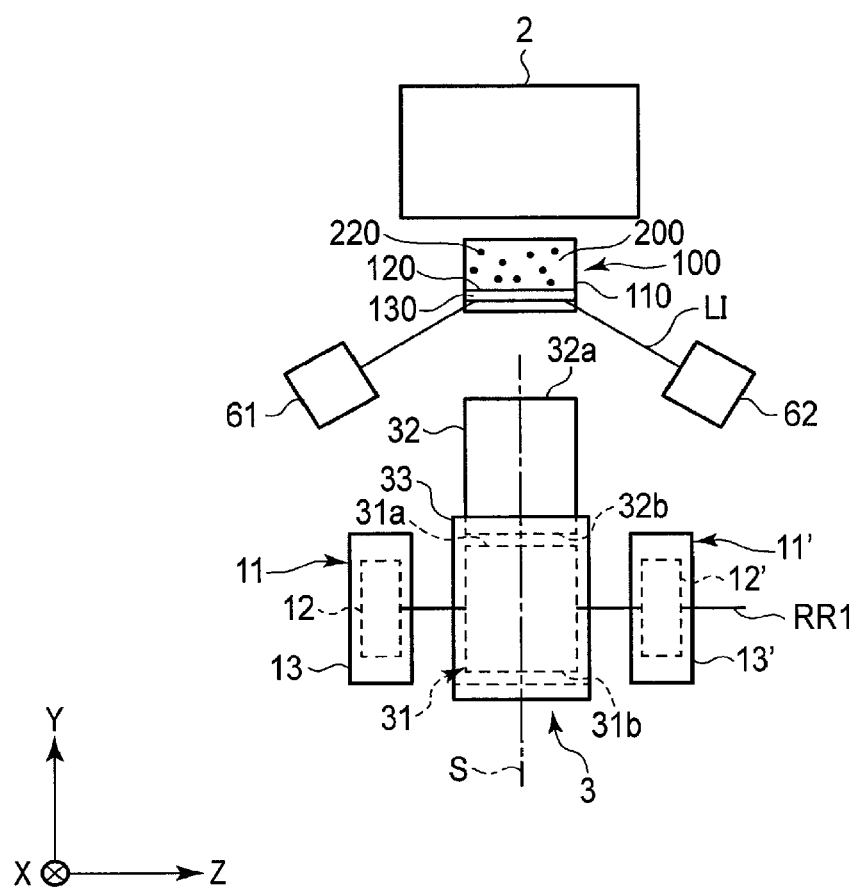
F I G. 17

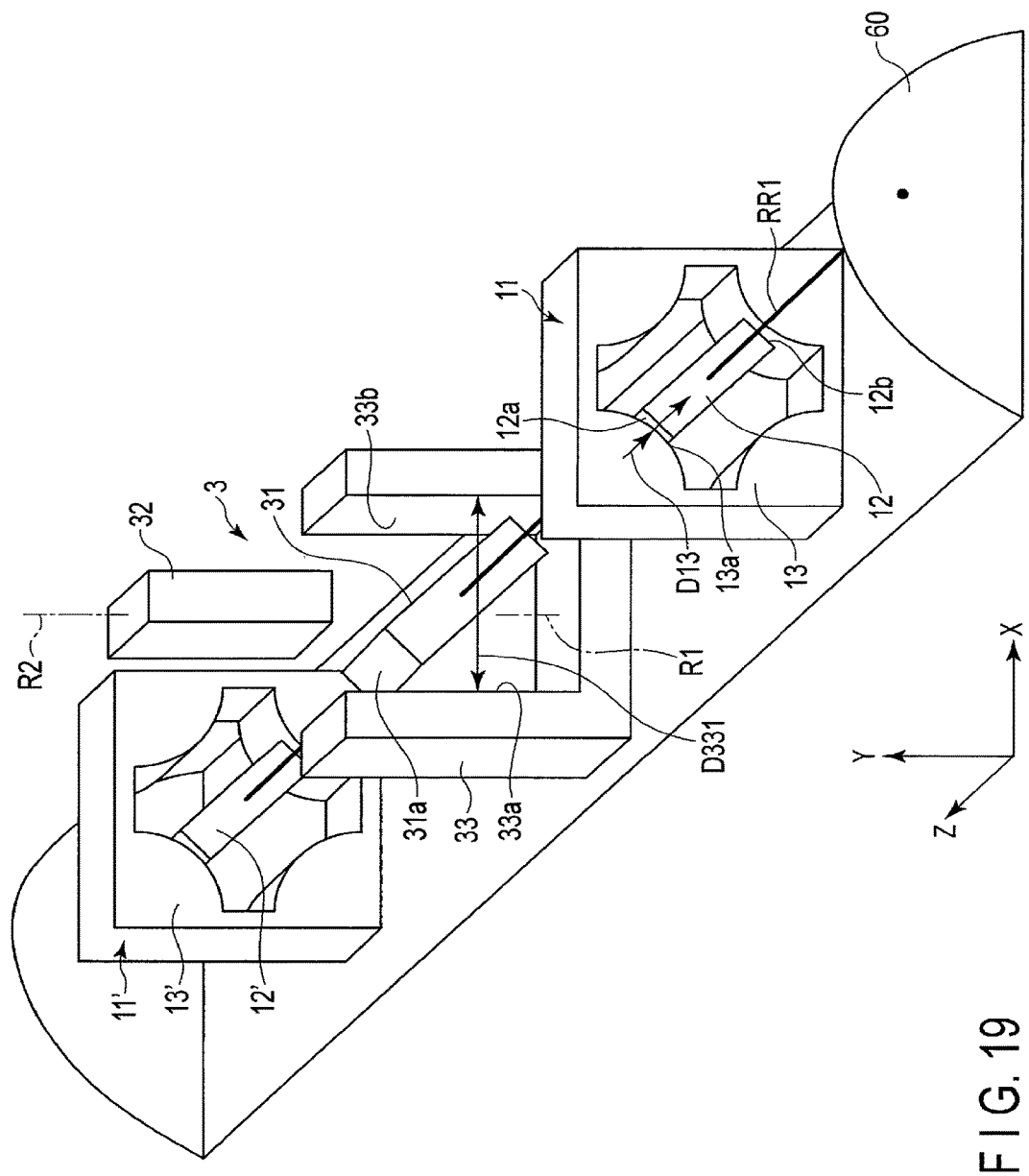
F I G. 19

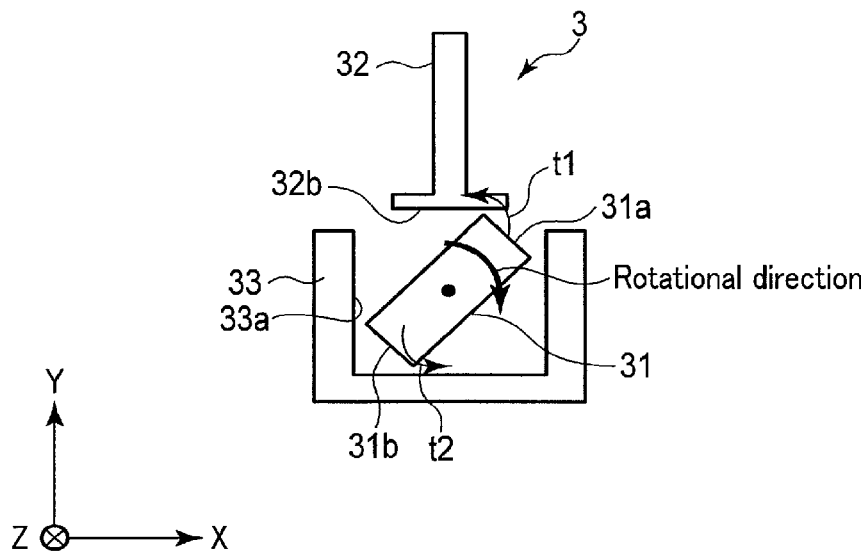
F I G. 20A
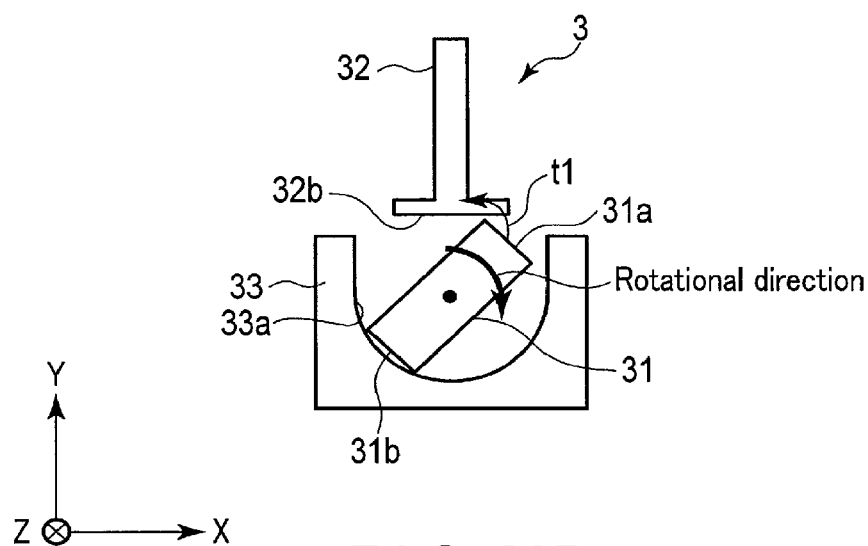
F I G. 20B

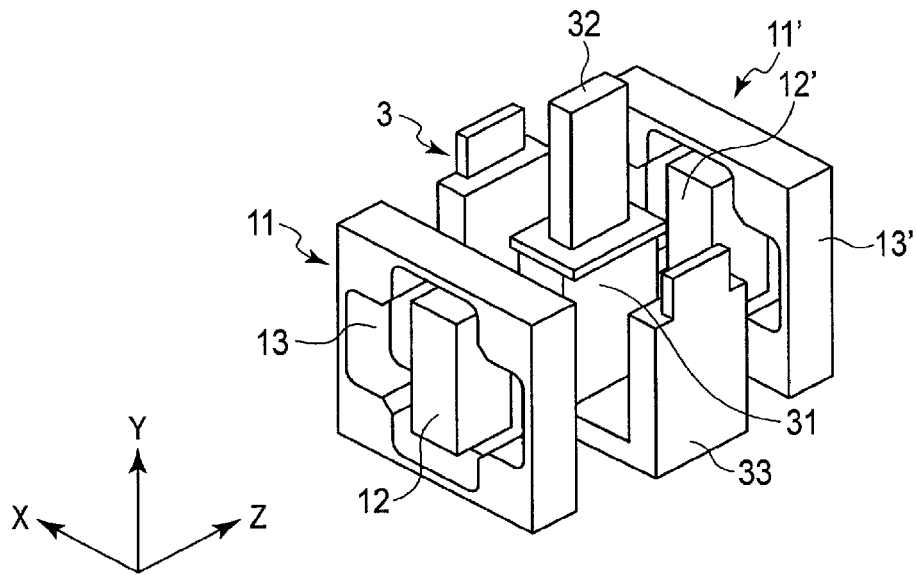
F I G. 21A
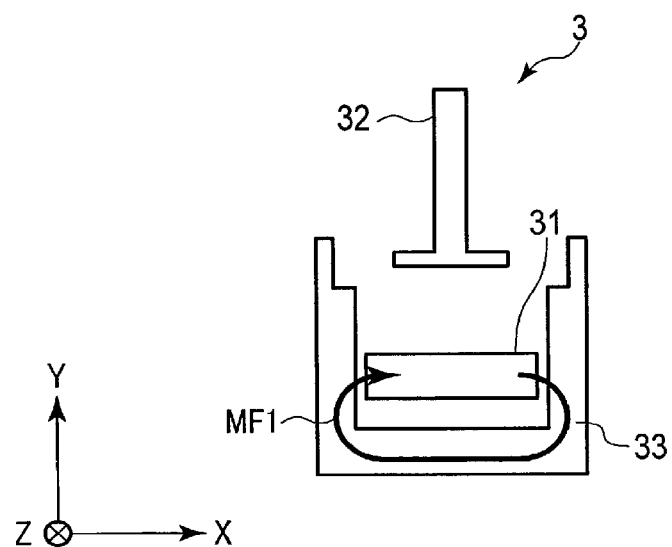
F I G. 21B

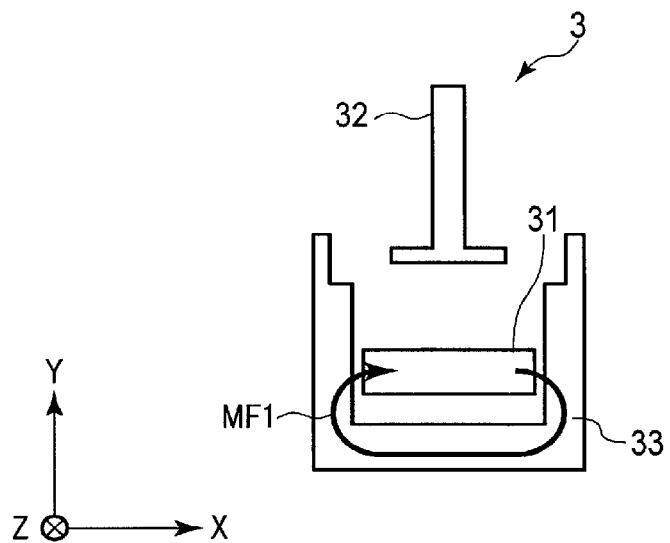
F I G. 22B
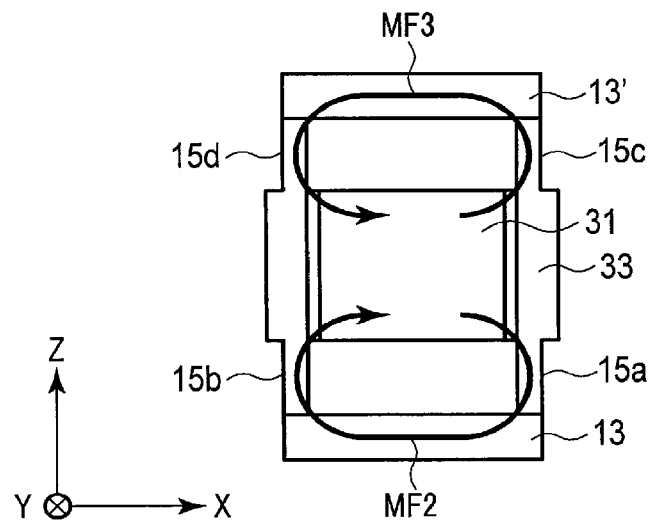
F I G. 22C

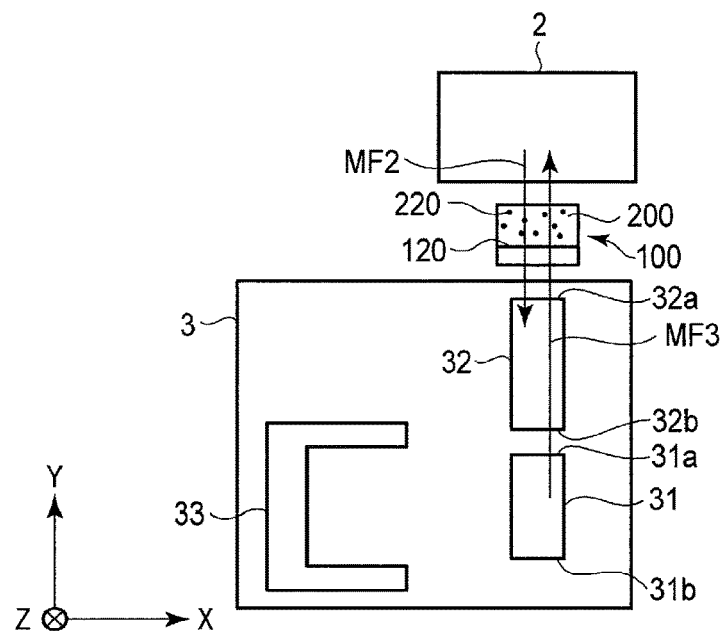
F I G. 23
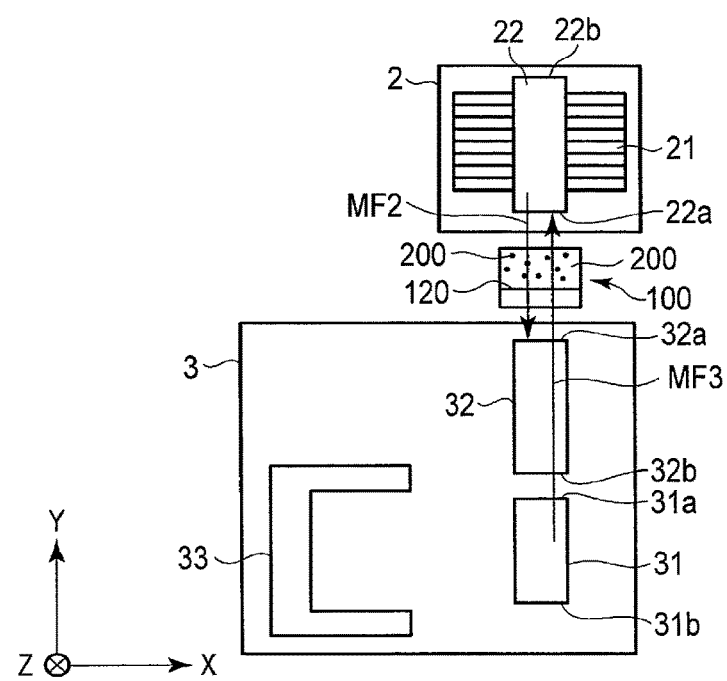
F I G. 24

SAMPLE ANALYZER

CROSS-REFERENCE TO RELATED APPLICATIONS

This application is based upon and claims the benefit of priority from the prior Japanese Patent Application No. 2015-203591, filed Oct. 15, 2015, the entire contents of which are incorporated herein by reference.

FIELD

Embodiments described herein relate generally to a sample analyzer.

BACKGROUND

Study has been conducted on a sample analyzer which detects a detection target molecule by utilizing a magnetic particle. As the magnetic particle, use is made of a magnetic microparticle which contains a magnetic material such as magnetite and is formed with a grain size of several-ten nm to several µm. It is known that such a magnetic particle has superparamagnetism. If a magnetic field is applied, the magnetic particles have magnetism, and move by magnetic force acting along a gradient of the magnetic field. If the magnetic field is shut off, the magnetic particles lose magnetism and are dispersed. The magnetic material, which constitutes the magnetic particles, has a greater specific gravity than water. Hence, if the content rate of magnetic material is large, the magnetic particles sediment and precipitate in a sample. Thus, the magnetic particle is formed by combining a magnetic material with a high-molecular material, so as to have such a composition that the specific gravity is made close to that of water. Furthermore, in order that the magnetic particle can specifically bond directly or indirectly to a specific detection target molecule, the magnetic particle is formed by chemically modifying the surface of the particle with a material, such as an antibody, which specifically bonds to the detection target molecule.

As the sample analyzer utilizing the magnetic particles as described above, there is known, for instance, an apparatus which switches the direction of movement of the magnetic particles by mechanically moving at least one magnet relative to a sensor cartridge. Specifically, the sensor cartridge is disposed between a pair of magnets which are provided such that their magnetic poles are opposed, and the paired magnets are mechanically moved at the same time relative to the sensor cartridge. In addition, there is known an apparatus in which a permanent magnet that applies a magnetic field to a sample is inserted into and drawn out of a C-shaped magnet by a moving mechanism such as a rotary disc, in order to switch ON/OFF of the magnetic field.

In this apparatus, in the state in which the permanent magnet for applying a magnetic field is disposed between the magnetic poles of the C-shaped magnet, the magnetic flux is closed between these two magnets, and the magnetic field, which is applied to the sample, can be reduced to substantially zero. However, in this structure, it is necessary to dispose the C-shaped magnet at a position away from a reaction container, so as to prevent the magnetic field formed by the C-shaped magnet from affecting the magnetic field distribution in the sample. Thus, the magnetic field generator including the moving mechanism of the permanent magnet becomes larger. In addition, since the C-shaped magnet and the permanent magnet for applying a magnetic field attract each other by magnetic force, an operation mechanism, which can exert a stronger force than the attractive force, is needed when the magnetic field is switched from ON to OFF. Furthermore, in this structure, when the magnetic field is switched from ON to OFF, the permanent magnet for magnetic field application is moved in parallel to a sensing area. Thus, due to this switching, magnetic particles collected to the sensing area are also dragged and moved, and the distribution of magnetic particles in the sensing area is distorted. Consequently, the efficiency of bond-reactions of magnetic particles with the sensing area surface deteriorates.

BRIEF DESCRIPTION OF THE DRAWING

FIG. 1 is a view illustrating the configuration of a sample analyzer according to the embodiment.

FIG. 2 is a view illustrating the arrangement of an upper magnetic field generator, a lower magnetic field generator, a cartridge and a detection device of FIG. 1.

FIG. 3 is a view illustrating the arrangement of the upper magnetic field generator, lower magnetic field generator and cartridge of the sample analyzer according to the embodiment.

FIG. 4A is a view for explaining the flow of a test of a detection target substance, which utilizes magnetic particles and is conducted under the control of magnetic field control circuitry of FIG. 1, FIG. 4A illustrating an arrangement in magnetic field ON by the lower magnetic field generator.

FIG. 5E is a view illustrating the lower magnetic field generator of FIG. 5D together with a housing.

FIG. 6A is a view illustrating the configuration of a lower magnetic field generator of a standard apparatus.

FIG. 6B is a view illustrating the configuration of a lower magnetic field generator of a permanent magnet apparatus according to the embodiment.

FIG. 7 is a graph illustrating time-based variations of light intensity signals relating to the standard apparatus and the permanent magnet apparatus according to the embodiment.

FIG. 8 is a graph illustrating reaction curves relating to samples of concentrations of three levels measured by the standard apparatus.

FIG. 9 is a graph illustrating reaction curves relating to samples of concentrations of three levels measured by the permanent magnet apparatus (sample analyzer) according to the embodiment.

FIG. 10 is a view illustrating the configuration of a sample analyzer according to application example 1 of the embodiment.

FIG. 11A is a view illustrating an arrangement in magnetic field ON of a slide-type lower magnetic field generator and a torque reducing magnetic circuit according to application example 1.

FIG. 12A is a view illustrating a detailed arrangement of the torque reducing magnetic circuit according to application example 1 of FIG. 11A to FIG. 11C.

FIG. 12B is a view illustrating a detailed arrangement of the torque reducing magnetic circuit according to application example 1 of FIG. 11A to FIG. 11C.

FIG. 12C is a view illustrating a detailed arrangement of the torque reducing magnetic circuit according to application example 1 of FIG. 11A to FIG. 11C.

FIG. 12D is a view illustrating a detailed arrangement of the torque reducing magnetic circuit according to application example 1 of FIG. 11A to FIG. 11C.

FIG. 12E is a view illustrating a detailed arrangement of the torque reducing magnetic circuit according to application example 1 of FIG. 11A to FIG. 11C.

FIG. 13A is a view illustrating a detailed arrangement of magnetic material components in magnetic field ON of a rotary-type lower magnetic field generator and a torque reducing magnetic circuit according to application example 1.

FIG. 13B is a view illustrating a detailed arrangement of the magnetic material components in magnetic field OFF of the rotary-type lower magnetic field generator and torque reducing magnetic circuit according to application example 1.

FIG. 13C is a view illustrating a detailed arrangement of the magnetic material components in a state between magnetic field ON and magnetic field OFF of the rotary-type lower magnetic field generator and torque reducing magnetic circuit according to application example 1.

FIG. 14A is a view illustrating the configuration of the lower magnetic field generator 3 (without a torque reducing magnetic circuit).

FIG. 14B is a view illustrating the configuration of the lower magnetic field generator 3 (with a torque reducing magnetic circuit).

FIG. 15 is a graph illustrating variations of torque due to the rotation of the permanent magnets in the magnetic circuits of FIG. 14A and FIG. 14B.

FIG. 16 is a view illustrating the configuration of a sample analyzer according to application example 2.

FIG. 17 is a view illustrating an arrangement of a cartridge, an upper magnetic field generator, a lower magnetic field generator, a torque reducing magnetic circuit and another torque reducing magnetic circuit according to application example 2.

FIG. 19 is a perspective view illustrating an arrangement of the lower magnetic field generator, the torque reducing magnetic circuit and the other torque reducing magnetic circuit, together with the housing.

FIG. 20A is a cross-sectional view illustrating the shape of an inner surface of a shunt yoke having a U shape.

FIG. 20B is a cross-sectional view illustrating the shape of an inner surface of a shunt yoke according to application example 3.

FIG. 21A is a perspective view of a lower magnetic field generator, a torque reducing magnetic circuit and another torque reducing magnetic circuit, which are not magnetically connected.

FIG. 21B is a view illustrating a magnetic flux in an overlapping manner on a transverse cross-sectional view of FIG. 21A at a time of magnetic field OFF.

FIG. 22B is a view illustrating a magnetic flux in an overlapping manner on a transverse cross-sectional view of FIG. 22A at a time of magnetic field OFF.

FIG. 22C is a plan view of FIG. 22B.

FIG. 23 is a view illustrating an arrangement and a magnetic flux of a sample analyzer according to application example 5.

FIG. 24 is a view illustrating a detailed arrangement and a magnetic flux of the sample analyzer according to application example 5.

DETAILED DESCRIPTION

Figure 4B:
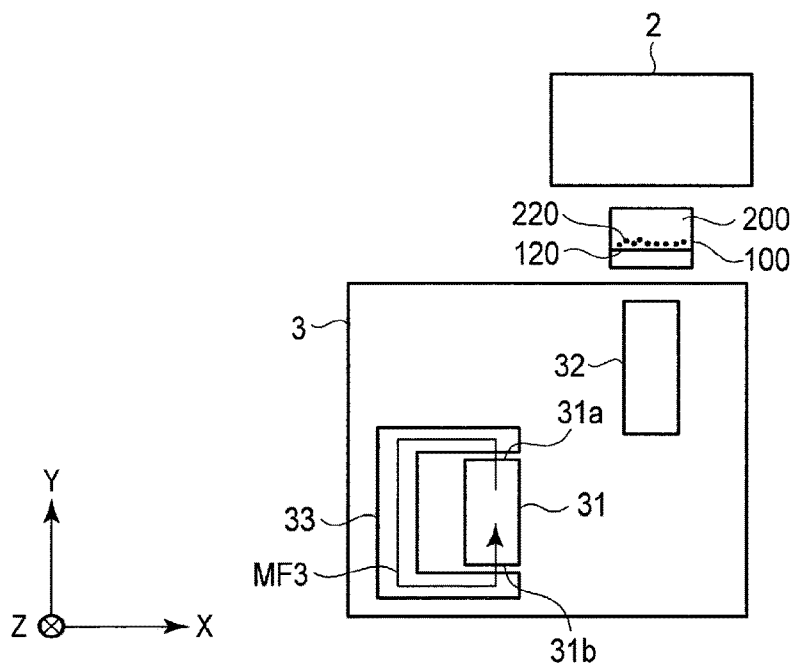
FIG. 4B is a view for explaining the flow of the test of the detection target substance, which utilizes magnetic particles and is conducted under the control of magnetic field control circuitry of FIG. 1, FIG. 4B illustrating an arrangement in magnetic field OFF.

In general, according to one embodiment, a sample analyzer includes a detector, a first magnetic field generator and a second magnetic field generator. The detector detects a target substance bonded to a magnetic particle which is included in a sample in a cartridge and collected to a sensing area in the cartridge. The first magnetic field generator is an apparatus configured to apply a first magnetic field for releasing the magnetic particles included in the sample from the sensing area. The first magnetic field generator is configured to be able to switch application and shut-off of the first magnetic field. The second magnetic field generator includes a first permanent magnet configured to generate a second magnetic field for attracting the magnetic particles included in the sample to the sensing area, a first soft magnetic material configured to be excited by the first permanent magnet, and a second soft magnetic material configured to short-circuit a magnetic flux from the first permanent magnet. The second magnetic field generator is configured to be able to switch application and shut-off of the second magnetic field by moving the first permanent magnet relative to the first soft magnetic material and the second soft magnetic material.

A sample analyzer according to the embodiment will be described hereinafter with reference to the accompanying drawings.

The sample analyzer according to the embodiment is an apparatus which analyzes a test target substance included in a sample such as a biological sample. To be more specific, the sample analyzer according to the embodiment optically detects the test target substance by utilizing magnetic particles.

FIG. 1 is a view illustrating the configuration of the sample analyzer according to the embodiment. As illustrated in FIG. 1, the sample analyzer according to the embodiment includes processing circuitry 1 as a central unit, an upper magnetic field generator 2, a lower magnetic field generator 3, a support frame 4, magnetic field control circuitry 5, a detection device 6, a display circuitry 7, an input circuitry 8, and a storage circuitry 9. The processing circuitry 1, magnetic field control circuitry 5, display circuitry 7, input circuitry 8 and storage circuitry 9 are connected to be mutually communicable via a bus.

The upper magnetic field generator 2 and lower magnetic field generator 3 are disposed such that a support frame 4 is interposed therebetween. The support frame 4 supports a cartridge 100. Specifically, the support frame 4 is a frame body which forms a predetermined space R1 in which the cartridge 100 is accommodated. The cartridge 100 is mounted on the support frame 4 and is disposed in the predetermined space R1. A sample is stored in the cartridge 100. The sample includes a sample, which includes a test target substance, and magnetic particles which are utilized for detecting the test target substance. An example of the test target substance is a biomolecule corresponding to a measurement item. A first substance, which specifically bonds to the test target substance, is fixed to the magnetic particle. A sensing area is provided on a bottom surface of the cartridge 100. A second substance, which specifically bonds to the test target substance, is fixed to the sensing area. The predetermined space R1 is located between the upper magnetic field generator 2 and lower magnetic field generator 3. The upper magnetic field generator 2 is a magnetic field generator which is disposed above the support frame 4, and the lower magnetic field generator 3 is a magnetic field generator which is disposed below the support frame 4. In accordance with the control by the magnetic field control circuitry 5, the upper magnetic field generator 2 generates a magnetic field which is applied to the sample stored in the cartridge 100. In accordance with the control by the magnetic field control circuitry 5, the lower magnetic field generator 3 generates a magnetic field which is applied to the sample stored in the cartridge 100. The lower magnetic field generator 3 is configured to be able to switch application and shut-off of the magnetic field to the sample.

The magnetic field control circuitry 5 controls the upper magnetic field generator 2 and lower magnetic field generator 3 synchronously, and switches application and shut-off of the magnetic field to the sample of each of the upper magnetic field generator 2 and lower magnetic field generator 3.

By alternately applying the magnetic field by the upper magnetic field generator 2 and lower magnetic field generator 3, the test target substance can efficiently be collected to the sensing area provided on the bottom surface of the cartridge 100. The magnetic field control circuitry 5 includes, as hardware resources, processors such as a CPU (Central Processing Unit) and an MPU (Micro Processing Unit), and memories such as a ROM (Read Only Memory) and a RAM (Random Access Memory). In addition, the magnetic field control circuitry 5 may be realized by an application specific integrated circuit (ASIC) configured to be capable of individually controlling the above generation timings, a field programmable gate array (FPGA), a complex programmable logic device (CPLD), or a simple programmable logic device (SPLD). The magnetic field control circuitry 5 is electrically connected to the upper magnetic field generator 2 and lower magnetic field generator 3 either by wire or wirelessly.

The detection device 6 detects the test target substance contained in the cartridge 100. The detection device 6 may detect the test target substance by any existing principle of optics, magnetism, electromagnetism, etc. For example, the detection device 6 according to this embodiment optically detects the test target substance. In this case, the detection device 6 radiates light to the cartridge 100, detects light propagating through the cartridge 100, and generates data corresponding to the intensity of detected light. The data of the detected light intensity is supplied to the processing circuitry 1, and is used for quantitative analysis of the test target substance.

The display circuitry 7 displays various data such as a quantitative analysis result of the test target substance. Specifically, the display circuitry 7 includes a display interface circuit and a display device. The display interface circuit converts data, which represents a display object, to a video signal. The video signal is supplied to the display device. The display device displays the video signal which represents the display object. As the display device, for example, a CRT display, a liquid crystal display, an organic EL display, an LED display, a plasma display, or an arbitrary display known in this technical field, may be used as needed.

The input circuitry 8 inputs various instructions from a user. Specifically, the input circuitry 8 includes an input device and an input interface circuit. The input device accepts various instructions from the user. The input device includes various switches, etc. The input interface circuit supplies an output signal from the input device to the processing circuitry 1 via the bus.

The storage circuitry 9 is a storage device such as an HDD (hard disk drive), an SSD (solid state drive), or an integrated circuit storage device, which stores various kinds of information. For example, the storage circuitry 9 stores data of a quantitative analysis result. In addition, the storage circuitry 9 stores control programs, etc. of the sample analyzer according to the embodiment.

The processing circuitry 1 includes, as hardware resources, processing devices (processors) such as a CPU and an MPU, and storage devices (memories) such as a ROM and a RAM. The processing circuitry 1 functions as a central unit of the sample analyzer according to the embodiment. Specifically, the processing circuitry 1 reads out a control program stored in the storage circuitry 9, develops the control program on the memory, and controls the respective components of the sample analyzer according to the developed control program. In addition, the processing circuitry 1 performs quantitative analysis on the data of detected light intensity, which was supplied from the detection device 6, and calculates the amount and concentration of the test target substance in the sample.

FIG. 2 is a view illustrating the arrangement of the upper magnetic field generator 2, lower magnetic field generator 3, cartridge 100 and detection device 6. As illustrated in FIG. 2, the upper magnetic field generator 2 is provided above the cartridge 100, and the lower magnetic field generator 3 is provided below the cartridge 100. Incidentally, in FIG. 2, depiction of the support frame 4 is omitted.

As illustrated in FIG. 2, the cartridge 100 includes a container 110, a sensing area 120 and a light guide 130. The container 110 is a container which stores a sample 200. As described above, the sample 200 is a solution including at least a sample, which includes a test target substance, and magnetic particles. A first substance, which specifically bonds to the test target substance, is fixed to the magnetic particle. The container 110 may preferably be formed by using a nonmagnetic material, so that the upper magnetic field generator 2 and lower magnetic field generator 3 can effectively apply magnetic fields to the sample 200. In addition, the material of the container 110 may preferably have such material quality that the container 110 is not corroded by the sample, a test reagent, etc. Specifically, it is desirable that the container 110 be formed by using an optical glass or a resin. The sensing area 120 is provided on the bottom surface of the container 110. A second substance, which specifically bonds to the test target substance, is fixed to the sensing area 120. Processing, such as coating for preventing nonspecific adsorption, may preferably be applied to the sensing area 120, so that the test target substance or magnetic particles 220 may not be nonspecifically fixed to the sensing area 120. The light guide 130 is coupled to the sensing area 120. The light guide 130 is formed of such a material as a thermosetting resin, a photo-curing resin, or glass. As the thermosetting resin, for example, use may be made of a phenol resin, an epoxy resin, an acrylic resin, etc.

As illustrated in FIG. 2, the detection device 6 optically detects the magnetic particles 220 which bond to the sensing area 120. Specifically, the detection device 6 includes a light source 61 and a photodetector 62. The light source 61 radiates light (hereinafter referred to as "detection light") LI to the light guide 130. As the light source 61, use may preferably be made of, for example, a diode such as an LED, or a lamp such as a xenon lamp. The detection light LI, which is incident on light guide 130, propagates while being total-reflected in the light guide 130, and is emitted from a predetermined emission port.

By the detection light LI which is total-reflected in the light guide 130, evanescent light occurs at an interface with the light guide 130 in the sensing area 120. The evanescent light is scattered or refracted by magnetic particles collected to the sensing area 120. The intensity of the detection light LI decreases in accordance with the amount of the scattered or refracted evanescent light. Specifically, the intensity of the detection light LI detected by the photodetector 62 varies depending on the amount of magnetic particles collected to the sensing area 120, or in other words, depending on the amount of the test target substance.

The photodetector 62 detects the detection light LI which is emitted from the light guide 130, and generates data of light detection intensity which indicates the intensity of the detection light LI that was detected. Under the light 130, there may be further provided a substrate which passes the detection light LI, or a grating for improving the efficiency of incidence of the detection light LI to the light guide 130.

In the meantime, as another method of optically detecting the test target substance, absorption/scattering of light by colored magnetic particles may be utilized. In this case, the detection device 6 detects the test target substance by selectively radiating light to the magnetic particles which are bonded to the sensing area 120, and detecting light from the magnetic particles. In addition, in order to magnetically detect the test target substance, the detection device 6 may include a magnetic sensor. By approaching the magnetic sensor to the sensing area 120, the magnetic sensor senses magnetic particles. As the magnetic sensor, use may be made of a Hall effect magnetic sensor, a magnetic impedance sensor, a giant magnetoresistive element, a SQUID (superconducting quantum interference device) magnetic sensor, etc.

Here, the height direction of the cartridge 100 is defined in a Y-axis direction, the lateral direction of the cartridge 100 is defined in an X-axis direction, and the depth direction of the cartridge 100 is defined in a Z-axis direction. The X-axis, Y-axis and Z-axis constitute an orthogonal three-dimensional coordinate system. In the present embodiment, the upper magnetic field generator 2, lower magnetic field generator 3, cartridge 100 and detection device 6 are arranged such that the Y-axis direction matches with the vertical direction. In this case, it is assumed that the upper magnetic field generator 2 is disposed upward along the Y-axis of the cartridge 100, and that the lower magnetic field generator 3 is disposed downward along the Y-axis of the cartridge 100.

Next, the details of the sample analyzer according to the embodiment will be described.

FIG. 3 is a view illustrating the arrangement of the upper magnetic field generator 2, lower magnetic field generator 3 and cartridge 100 of the sample analyzer according to the embodiment. As illustrated in FIG. 3, the lower magnetic field generator 3 is disposed near the sensing area 120 of the cartridge 100, and the upper magnetic field generator 2 is disposed away from the sensing area 120. By arranging the upper magnetic field generator 2 and lower magnetic field generator 3 in this manner, the upper magnetic field generator 2 and lower magnetic field generator 3 can apply to the sample stored in the cartridge 100 the magnetic field for releasing the magnetic particles 220 from the sensing area 120 and the magnetic field for attracting the magnetic particles 220 to the sensing area 120, and can also shut off the magnetic field.

The lower magnetic field generator 3 includes a permanent magnet (first permanent magnet) 31, a core (first soft magnetic material) 32 and a shunt yoke (second soft magnetic material) 33. The permanent magnet 31 has a columnar shape such as a circular columnar shape, a rectangular columnar shape or a plate shape. The permanent magnet 31 generates a magnetic field. The permanent magnet 31 includes a pair of magnetic poles. That surface of the permanent magnet 31, which has a first magnetic pole, is referred to as "first magnetic pole surface 31a", and that surface of the permanent magnet 31, which has a second magnetic pole, is referred to as "second magnetic pole surface 31b". As the permanent magnet 31, any kind of existing permanent magnets may be used, such as a ferrite magnet, an alnico magnet, a samarium-cobalt magnet, or a neodymium magnet. In particular, a rare-earth magnet, such as a samarium magnet or neodymium magnet, has a large residual magnetic flux density, and can impart a high magnetic flux density to the sample 200. Incidentally, either the first magnetic pole or the second magnetic pole may be an N pole or an S pole.

The core 32 is a soft magnetic body formed of a soft magnetic material which is fixed between the sensing area 120 and the permanent magnet 31. The core 32 has a columnar shape such as a circular columnar shape, a rectangular columnar shape or a plate shape. The core 32 undergoes magnetic seeding by the permanent magnet 31 in order to apply a magnetic field to the sample 200 in the cartridge 100. A surface 32a of the core 32, which is opposed to the sensing area 120, has substantially the same size and shape as the sensing area 120. In addition, a surface 32b of the core 32, which is opposed to the permanent magnet 31, has a size and a shape, which are equal to or greater than the size and shape of the magnetic pole surface (31a, 31b) of the permanent magnet 31. Since the core 32 with the above disposition and shape is provided, the magnetic flux from the permanent magnet 31 can be passed through the core 32 by approaching the magnetic pole 31a or 31b of the permanent magnet 31 to the core 32, and the magnetic flux from the core 32 can be passed through the sample 200. Thereby, the magnetic field can be applied to the sample 200. In short, the permanent magnet 31 and core 32 constitute a magnetic circuit for applying the magnetic field to the sample 200.

The shunt yoke 33 is a soft magnetic body formed of a soft magnetic material which is spaced apart from the core 32. The shunt yoke 33 short-circuits the magnetic flux from the permanent magnet 31 in order to shut off the magnetic field to the sample 200. By forming the shunt yoke 33 of the soft magnetic material, the magnetism that the shunt yoke 33 retains can be reduced to substantially zero in the state in which the permanent magnet 31 is spaced apart from the shunt yoke 33. Specifically, the magnetic effect, which the shunt yoke 33 exerts on the space in the cartridge 100, can be ignored. The shunt yoke 33 has a C shape or a U shape. Corner portions of the shunt yoke 33 may be angular or curved. A distance D331 between mutually opposed surfaces of projecting portions at both ends of the shunt yoke 33 is designed to be slightly greater than a distance D31 between the magnetic pole surfaces 31a and 31b of the permanent magnet 31. Since the shunt yoke 33 has the above-described shape and dimension, the shunt yoke 33 can sandwich the permanent magnet 31. If the shunt yoke 33 sandwiches the permanent magnet 31, the magnetic flux generated from the permanent magnet 31 passes through the shunt yoke 33. Thereby, the permanent magnet 31 and shunt yoke 33 constitute a closed circuit, and the magnetic flux generated from the permanent magnet 31 can be short-circuited.

As described above, the lower magnetic field generator 3 according to the embodiment includes the permanent magnet 31 configured to generate a magnetic field for attracting the magnetic particles 220 included in the sample 200 to the sensing area 120; the core 32 configured to be excited by the permanent magnet 31; and the shunt yoke 33 configured to short-circuit the magnetic flux from the permanent magnet 31. By moving the permanent magnet 31 relative to the core 32 and the shunt yoke 33, the lower magnetic field generator 3 switches the application and shut-off of the magnetic field.

Figure 4C:
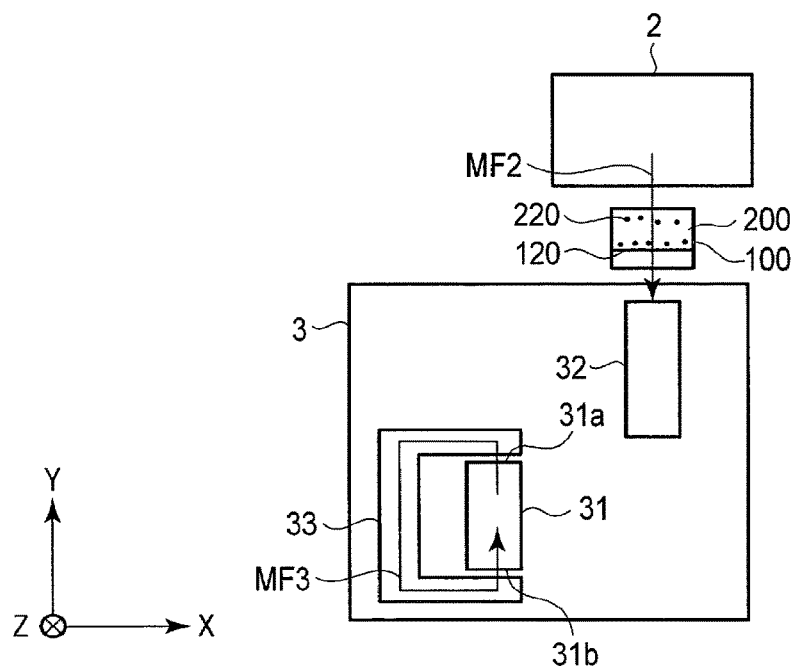
FIG. 4C is a view for explaining the flow of the test of the detection target substance, which utilizes magnetic particles and is conducted under the control of magnetic field control circuitry of FIG. 1, FIG. 4C illustrating an arrangement in magnetic field ON by the upper magnetic field generator.

Next, referring to FIG. 4A, FIG. 4B and FIG. 4C, a description is given of the flow of the test of the detection target substance, which utilizes magnetic particles and is conducted under the control of magnetic field control circuitry 5. FIG. 4A illustrates a configuration at a time when the magnetic field is applied by the lower magnetic field generator 3. FIG. 4B illustrates a configuration at a time when the magnetic field is shut off. FIG. 4C illustrates a configuration at a time when the magnetic field is applied by the upper magnetic field generator 2.

The magnetic field control circuitry 5 controls the upper magnetic field generator 2 and lower magnetic field generator 3, and causes the upper magnetic field generator 2 and lower magnetic field generator 3 to cause the magnetic particles 220 included in the cartridge 100 to alternately approach, and move away from, the sensing area 120. The test utilizing the magnetic particles 220 is conducted by the following processes. Process 1: as illustrated in FIG. 4A, a magnetic field for attracting the magnetic particles 220, which are dispersed in the sample 200, to the sensing area 120 is applied to the sample 200. Process 2: as illustrated in FIG. 4B, the magnetic field is shut off in order to cause the magnetic particles 220, which are collected to the vicinity of the sensing area 120, to specifically bond to the sensing area 120. Process 3: a magnetic field for releasing the magnetic particles 220, which did not specifically bond to the sensing area 120, from the sensing area 120 is applied to the sample 200.

Hereinafter, the test utilizing the magnetic particles will be described in detail.

To start with, in the state in which the upper magnetic field generator 2 and lower magnetic field generator 3 are turned off, the magnetic particles 220 are reacted with the detection target substance in the sample 200.

Next, process 1 is performed. In process 1, the magnetic particles 220, which are dispersed in the whole of the sample 200, are collected to the sensing area 120. If a strong magnetic force can be made to act on the magnetic particles 220, the magnetic particles 220 can be collected quickly and efficiently, and the test time can be shortened. The magnetic force acting on the magnetic particles 220 is proportional to the product of the specific magnetic susceptibility of magnetic particles 220, the magnetic flux density of magnetic field and the magnetic flux density gradient, and acts in a direction of the magnetic flux density gradient (in a direction from a small magnetic flux density to a large magnetic flux density). Thus, in order to shorten the test time, it is effective to adopt such configuration that, in the state in which the magnetic field is applied, the magnetic flux density is high and the gradient of magnetic flux density is large in the sample 200.

In process 1, the magnetic field control circuitry 5 supplies an ON signal to the lower magnetic field generator 3 in order to turn on the magnetic field from the lower magnetic field generator 3. Upon receiving the ON signal supplied from the magnetic field control circuitry 5, the lower magnetic field generator 3 applies the magnetic field to the sample 200. Specifically, as illustrated in FIG. 4A, the lower magnetic field generator 3 moves one magnetic pole 31a of the permanent magnet 31 in a manner to approach the core 32. By the magnetic pole 31a approaching the core 32, a magnetic flux MF3, which is generated from the permanent magnet 31, passes through the core 32, and is guided to the sample 200 that is located on that side of the core 32, which is opposite to the permanent magnet 31. Since the lower magnetic field generator 3 is disposed near the sensing area 120 of the cartridge 100, the magnetic flux density in the sample 200 is higher on the sensing area 120 side in the state in which the lower magnetic field generator 3 is ON. Thus, the magnetic particles 220 approach the sensing area 120. The magnetic field from the lower magnetic field generator 3 is applied during a predetermined time. The application of the magnetic field from the lower magnetic field generator 3 may be automatically executed upon being triggered by the passage of a predetermined time from the start of the test, or may be executed at a timing instructed by the user through the input circuitry 8.

Next, process 2 is performed. In process 2, it is desirable that the magnetic field that is applied be substantially zero at least in the vicinity of the sensing area 120. If the magnetic field is applied in the state in which many magnetic particles exist near the sensing area 120, the magnetized magnetic particles would agglomerate due to a magnetic interaction. Consequently, if the magnetic field remains applied, the magnetic particles, which can approach the nearest point to the surface of the sensing area 120 is only a part of the collected magnetic particles, and the bond-reaction efficiency between the magnetic particles and the second substance on the sensing area 120 remains low. After the magnetic particles are collected to the vicinity of the sensing area 120, the magnetic field in the vicinity of the sensing area 120 is shut off. Thereby, the magnetism of the magnetic particles is lost, the agglomeration is eliminated, and most of the magnetic particles sediment on the surface of the sensing area 120 due to gravitational force. Hence, the bond-reaction between the magnetic particles and the second substance of the sensing area 120 is promoted.

In process 2, after a predetermined time has passed since the application of the magnetic field from the lower magnetic field generator 3 was started, the magnetic field control circuitry 5 supplies an OFF signal to the lower magnetic field generator 3 in order to turn off the magnetic field. Upon receiving the supplied OFF signal, the lower magnetic field generator 3 approaches the magnetic poles 31a and 31b of the permanent magnet 31 to the shunt yoke 33, as illustrated in FIG. 4B. As a result, the magnetic flux MF3, which is generated from the permanent magnet 31, forms such a closed loop that the magnetic flux MF3 passes through the shunt yoke 33 and returns to the permanent magnet 31. In this manner, by approaching the magnetic poles 31a and 31b of the permanent magnet 31 to the shunt yoke 33, the magnetic field that is applied to the sample 200 is shut off. By shutting off the magnetic field, the magnetic field near the sensing area 120 becomes substantially zero. In this state, the bond-reaction is caused to occur between the magnetic particles 220 and the second substance bonded to the sensing area 120.

Next, process 3 is performed. In process 3, a magnetic field having a gradient in an opposite direction to the gradient in process 1 is applied in order to release from the sensing area 120 the magnetic particles which exist on the sensing area 120 but are not bonded to the sensing area 120, that is, the non-reacted magnetic particles which are not bonded to the detection target substance.

In process 3, the magnetic field control circuitry 5 supplies an ON signal to the upper magnetic field generator 2 in order to turn on the magnetic field from the upper magnetic field generator 2. Upon receiving the ON signal supplied from the magnetic field control circuitry 5, the upper magnetic field generator 2 generates a magnetic field. A magnetic field MF2 from the upper magnetic field generator 2 passes through the sample 200. Thereby, the magnetic field from the upper magnetic field generator 2 is applied to the sample 200. As illustrated in FIG. 4C, compared to the lower magnetic field generator 3, the upper magnetic field generator 2 is disposed at a position far from the sensing area 120. Thus, if the magnetic field from the lower magnetic field generator 3 is turned off and the magnetic field from the upper magnetic field generator 2 is turned on, the magnetic flux density in the sample 200 becomes lower on the sensing area 120 side. Thus, the magnetic particles 220 move in a direction away from the sensing area 120.

Thereafter, the detection target substance, which is bonded to the magnetic particles 220 on the sensing area 120, is optically measured by the detection device 6.

Figure 5A:
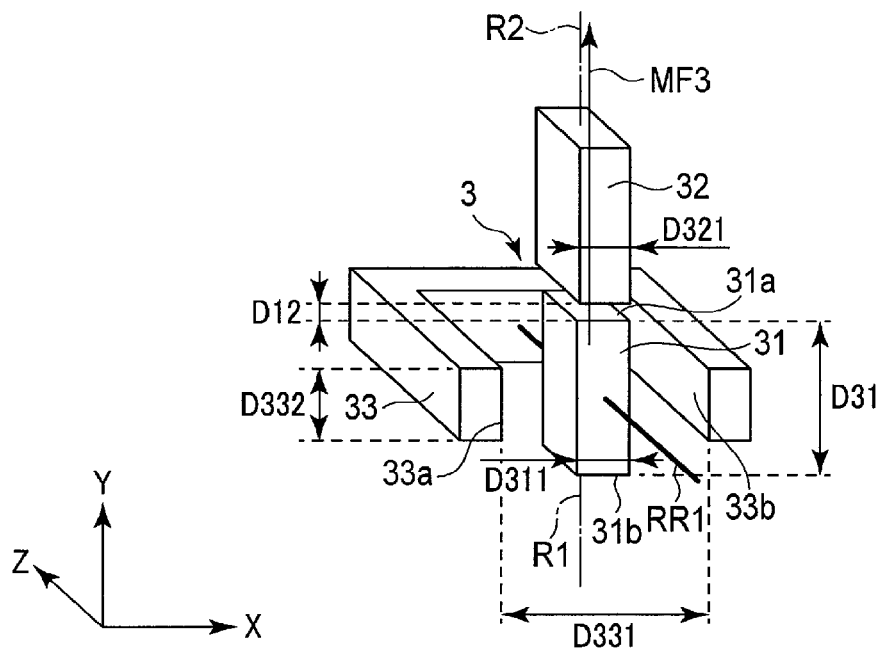
FIG. 5A is a view illustrating an arrangement of magnetic material components and a magnetic flux at a time of magnetic field application of the lower magnetic field generator according to the embodiment.
Figure 5B:
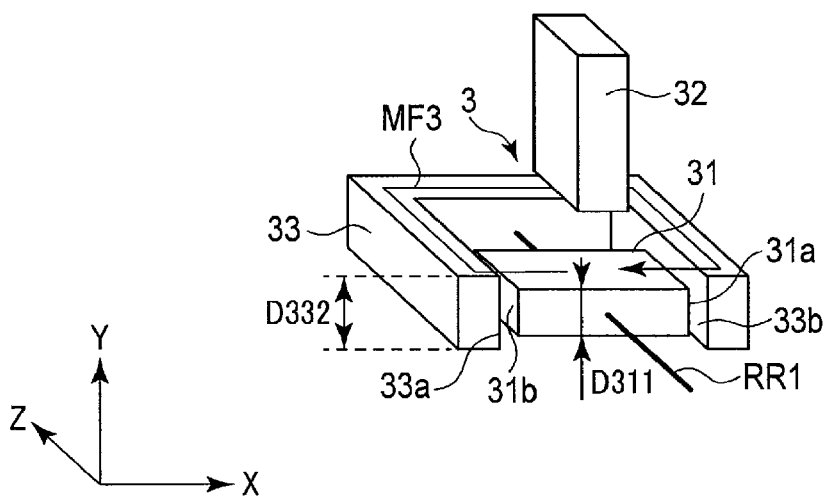
FIG. 5B is a view illustrating the arrangement of the magnetic material components and magnetic flux at a time of magnetic field shut-off of the lower magnetic field generator according to the embodiment.
Figure 5C:
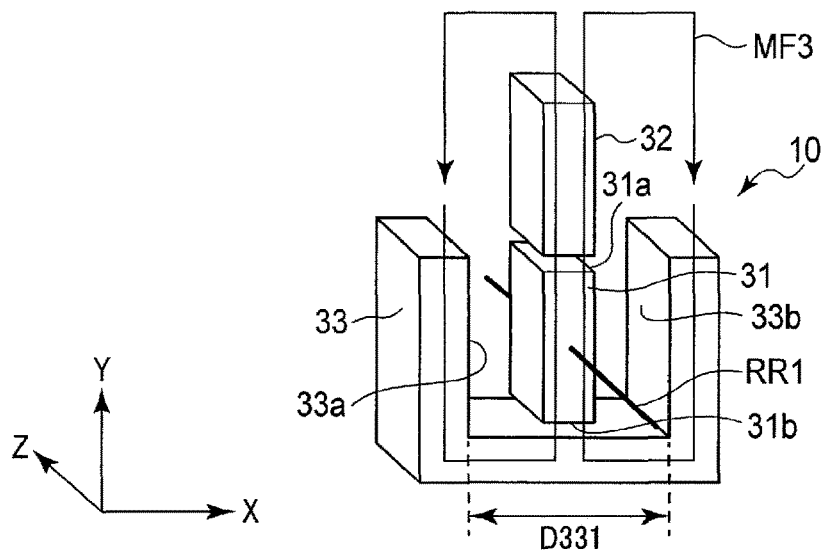
FIG. 5C is a view illustrating an arrangement of magnetic material components and a magnetic flux, which are different from those in FIG. 5A, at a time of magnetic field application of the lower magnetic field generator according to the embodiment.
Figure 5D:
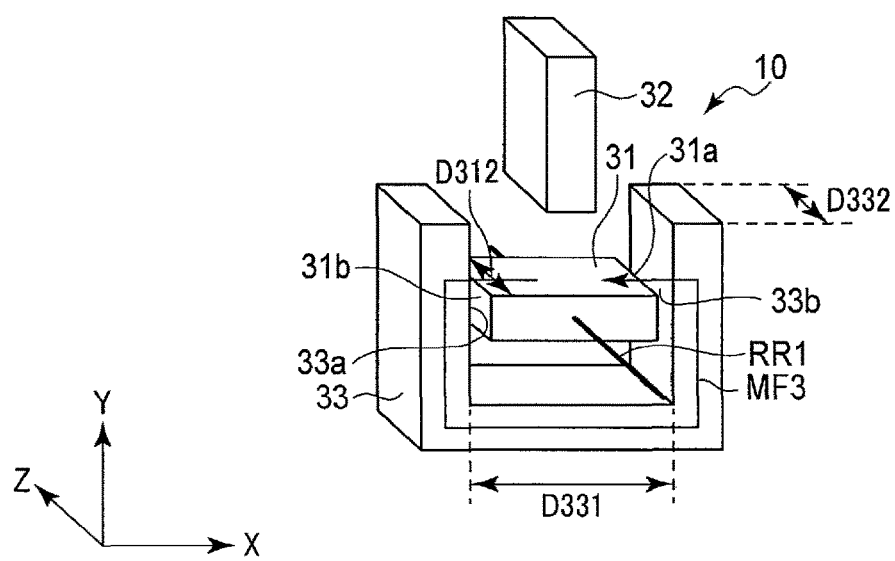
FIG. 5D is a view illustrating an arrangement of the magnetic material components and magnetic flux, which are different from those in FIG. 5B, at a time of magnetic field shut-off of the lower magnetic field generator according to the embodiment.

Next, referring to FIG. 5A, FIG. 5B, FIG. 5C and FIG. 5D, a description is given of the details of the lower magnetic field generator 3 according to the embodiment. FIG. 5A and FIG. 5B illustrate an example of the lower magnetic field generator 3 in which a rotational axis RR1 of the permanent magnet 31 is disposed in the same plane as the shunt yoke 33. In other words, the rotational axis RR1 of the permanent magnet 31 is disposed substantially perpendicular to the center axis (not shown) of the shunt yoke 33. FIG. 5A is a view illustrating the arrangement and magnetic flux of the lower magnetic field generator 3 at a time of magnetic field application. FIG. 5B is a view illustrating the arrangement and magnetic flux of the lower magnetic field generator 3 at a time of magnetic field shut-off. FIG. 5C and FIG. 5D illustrate an example of the lower magnetic field generator 3 in which the rotational axis RR1 of the permanent magnet 31 is disposed in a manner to traverse the shunt yoke 33. In other words, the rotational axis RR1 of the permanent magnet 31 is disposed to substantially agree with the center axis (not shown) of the shunt yoke 33. FIG. 5C is a view illustrating the arrangement and magnetic flux of the lower magnetic field generator 3 at a time of magnetic field application. FIG. 5D is a view illustrating the arrangement and magnetic flux of the lower magnetic field generator 3 at a time of magnetic field shut-off.

As described above, the core 32 is fixed between the cartridge (not shown) and the permanent magnet 31, and the shunt yoke 33 is disposed in a manner to sandwich the permanent magnet 31. The permanent magnet 31 is configured to be rotatable about the rotational axis RR1. As illustrated in FIG. 5A, FIG. 5B, FIG. 5C and FIG. 5D, by the permanent magnet 31 rotating about the rotational axis RR1, the ON/OFF of the magnetic field, which is applied from the permanent magnet 31 to the sample 200 via the core 32, can be switched. Any configuration may be adopted as the configuration for making the permanent magnet 31 rotatable about the rotational axis RR1. For example, the permanent magnet 31 may preferably be supported by a support frame (not shown) so as to be rotatable about the rotational axis RR1. In addition a rotational shaft may preferably be fixed directly to the permanent magnet 31 such that the permanent magnet 31 rotates about the rotational axis RR1. In addition the rotational axis RR1 is connected to, for example, a driving device such as a servo motor (not shown), and the driving device receives an ON signal or an OFF signal from the magnetic field control circuitry 5, and rotates the permanent magnet 31 about the rotational axis RR1 by a predetermined rotational angle. Incidentally, the rotational axis RR1 is an imaginary axis. Here, "imaginary" means that the rotational axis RR1 is not necessarily required to actually penetrate the permanent magnet 31 as a physical structural element.

As illustrated in FIG. 5A and FIG. 5C, the permanent magnet 31 and core 32 are disposed such that a longitudinal axis R1 extending through the N pole and S pole of the permanent magnet 31 matches with a longitudinal axis R2 of the core 32. In addition, the permanent magnet 31 is disposed such that the longitudinal axis R1 thereof is perpendicular to the rotational axis RR1. The permanent magnet 31 and core 32 are disposed with such a distance D12 that the permanent magnet 31 does not come in contact with the core 32 when the permanent magnet 31 rotates about the rotational axis RR1. The shunt yoke 33 has a C shape or a U shape. The shunt yoke 33 and permanent magnet 31 are positioned such that the rotational axis RR1 intersects at right angles with a substantially central point of a distance D331 of an opening of the shunt yoke 33 (a space surrounded by the shunt yoke 33). In other words, the distance D331 is equal to a distance between an inner surface 33a and an inner surface 33b which are opposed to each other with the opening of the shunt yoke 33 interposed.

As illustrated in FIG. 5B and FIG. 5D, the distance D331 of the opening of the shunt yoke 33 is designed to be greater than a length D31 along the longitudinal axis R1 of the permanent magnet 31, such that the permanent magnet 31 does not come in contact with the shunt yoke 33 when the permanent magnet 31 rotates about the rotational axis RR1. In addition, as illustrated in FIG. 5B, the distance D331 is designed such that, when the permanent magnet 31 is disposed with the longitudinal axis R1 of the permanent magnet 31 intersecting at right angles with the longitudinal axis R2 of the core 32, the shunt yoke 33 and the magnetic poles 31a and 31b come in close proximity so that the magnetic flux from the permanent magnet 31 passes through the shunt yoke 33 without leakage.

As illustrated in FIG. 5A, FIG. 5B, FIG. 5C and FIG. 5D, the permanent magnet 31 is disposed in the opening of the shunt yoke 33. Specifically, in the case of the arrangement illustrated in FIG. 5A and FIG. 5B, the permanent magnet 31 is disposed in the opening of the shunt yoke 33 such that the rotational axis RR1 penetrates the shunt yoke 33. In other words, in the case of the arrangement illustrated in FIG. 5C and FIG. 5D, the permanent magnet 31 is disposed in the opening of the shunt yoke 33 such that the rotational axis RR1 does not penetrate the shunt yoke 33.

As illustrated in FIG. 5A and FIG. 5C, the permanent magnet 31 may preferably be designed and disposed such that the magnetic pole 31a of the permanent magnet 31, which is in close proximity to the core 32, projects out of the opening of the yoke 33 when a magnetic field is applied to the sample. For example, as illustrated in FIG. 5A, in the lower magnetic field generator 3 in which the rotational axis RR1 of the permanent magnet 31 is disposed in the same plane as the shunt yoke 33, the distance D31 along the longitudinal axis R1 of the permanent magnet 31 may preferably be designed to be greater than a width D332 of the inner surface 33a, 33b of the shunt yoke 33. In addition, as illustrated in FIG. 5C, in the lower magnetic field generator 3 in which the rotational axis RR1 of the permanent magnet 31 is disposed in a manner to traverse the shunt yoke 33, the permanent magnet 31 and rotational axis RR1 may preferably be disposed such that the magnetic pole 31a of the permanent magnet 31, which is in close proximity to the core 32, projects above the upper end of the shunt yoke 33 when the magnetic field is applied to the sample. If the magnetic pole 31a of the permanent magnet 31, which is in close proximity to the core 32, does not project out of the opening of the shunt yoke 33, part of the magnetic flux, which is generated from the permanent magnet 31, would enter not the core 32 but the shunt yoke 33. Consequently, the magnetic force of the magnetic field, which is applied to the sample in the cartridge 100, would decrease. As described above, when the magnetic pole 31a of the permanent magnet 31, which is in close proximity to the core 32, projects out of the opening of the shunt yoke 33, most of the magnetic flux, which is generated from the permanent magnet 31, can be made to pass through the core 32. Thereby, it is possible to prevent a decrease of the magnetic force of the magnetic field which is applied to the sample in the cartridge 100.

As illustrated in FIG. 5B and FIG. 5D, when the magnetic field from the permanent magnet 31 to the sample is shut off, the permanent magnet 31 and shunt yoke 33 may preferably be designed and disposed such that the permanent magnet 31 is included in the inside of the opening of the shunt yoke 33. As illustrated in FIG. 5B, in the lower magnetic field generator 3 in which the rotational axis RR1 of the permanent magnet 31 is disposed in the same plane as the shunt yoke 33, a thickness of the magnetic pole surface 31a, 31b of the permanent magnet 31 (a length along the axis perpendicular to the rotational axis RR1 and longitudinal axis R1) D311 may preferably be designed to be less than the width D332 of the shunt yoke 33. If the thickness D311 of the magnetic pole surface 31a, 31b is greater than the width D332 of the shunt yoke 33, part of the magnetic flux, which is generated from the permanent magnet 31, would enter not the yoke 33 but the core 32. Consequently, the capability of shut-off of the magnetic field, which is applied to the sample in the cartridge 100, would deteriorate. As described above, when the thickness D311 of the magnetic pole surface 31a, 31b is less than the width D332 of the shunt yoke 33, most of the magnetic flux, which is generated from the permanent magnet 31, can be made to pass through the shunt yoke 33. Thereby, it is possible to improve the capability of shut-off of the magnetic field which is applied to the sample in the cartridge 100. In addition, as illustrated in FIG. 5D, in the lower magnetic field generator 3 in which the rotational axis RR1 of the permanent magnet 31 is disposed in a manner to traverse the shunt yoke 33, a thickness D312 of the magnetic pole surface 31a, 31b of the permanent magnet 31 in a direction parallel to the rotational axis RR1, may preferably be designed to be less than the width D332 of the shunt yoke 33.

Next, a description is given of the ON/OFF switching operation of the magnetic field by the above-described lower magnetic field generator 3. When a magnetic field is turned on, the magnetic field control circuitry 5 supplies an ON signal to a driving device (not shown) in the lower magnetic field generator 3. As illustrated in FIG. 5A or FIG. 5C, the driving device rotates the permanent magnet 31 about the rotational axis RR1, and approaches the magnetic pole surface 31a or 31b to the bottom surface 32b of the core 32. In other words, the longitudinal axis R1 of the permanent magnet 31 is made to agree with the longitudinal axis R2 of the core 32. At this time, the magnetic flux MF3, which is generated from the permanent magnet 31, passes through the core 32, and is applied to the sample 200 stored in the cartridge 100 that is located on the opposite side of the core 32.

When the magnetic field is turned off, the magnetic field control circuitry 5 supplies a magnetic field shut-off signal to the driving device (not shown) in the lower magnetic field generator 3. As illustrated in FIG. 5B or 5D, the driving device rotates the permanent magnet 31 about the rotational axis RR1, and approaches the magnetic pole surfaces 31a and 31b to the shunt yoke 33. To be more specific, the driving device makes the longitudinal axis R1 of the permanent magnet 31 perpendicular to the longitudinal axis R2 of the core 32. By this rotation, the magnetic poles 31a and 31b are opposed to the inner surfaces of the shunt yoke 33. At this time, the magnetic flux MF3, which is generated from the permanent magnet 31, forms such a closed loop that the magnetic flux MF3 passes through the shunt yoke 33 and returns to the permanent magnet 31. Thus, most of the magnetic flux is not guided to the core 32, and the magnetic field, which is applied to the inside of the cartridge 100, is substantially shut off.

In the meantime, FIG. 5A, FIG. 5B, FIG. 5C and FIG. 5D illustrate the arrangement of magnetic material components which are minimum necessary components of the magnetic circuit of the lower magnetic field generator 3. Actually, the core 32 and shunt yoke 33 are mechanically fixed in a unit by a nonmagnetic structure. For example, FIG. 5E is a view illustrating the lower magnetic field generator 3 of FIG. 5D together with a housing 50. As illustrated in FIG. 5E, the core 32 is supported by the housing 50. The housing 50 has a substantially C shape or U shape, and is disposed in a manner to straddle the permanent magnet 31 and shunt yoke 33. The core 32 is disposed on the housing 50 such that the core 32 is fixed above the permanent magnet 31. The housing 50 is formed of a nonmagnetic material such as brass or aluminum. Besides, an additional yoke may be provided as a structural element of the lower magnetic field generator 3.

Next, a description is given of a comparison between the sample analyzer according to the embodiment (hereinafter referred to as "permanent magnet apparatus") and a standard sample analyzer (hereinafter "standard apparatus").

FIG. 6A is a view illustrating the configuration of a lower magnetic field generator 270 of the standard apparatus. An electromagnet 272 is used in the lower magnetic field generator 270 of the standard apparatus. A magnetic flux, which is generated by the electromagnet 272, is applied to the cartridge via a core 271, and returns to a yoke 273 via an upper magnetic field generator (not shown). In the lower magnetic field generator 270 of the standard apparatus, the ON/OFF of the magnetic field is controlled by the supply of power to the electromagnet 272.

FIG. 6B is a view illustrating the configuration of the lower magnetic field generator 3 of the permanent magnet apparatus according to the embodiment. The lower magnetic field generator 3 is a device in which a permanent magnet is substituted for the electromagnet that is mounted in the standard apparatus. The lower magnetic field generator 3 illustrated in FIG. GB includes another yoke 34, in addition to the core 32, permanent magnet 31 and shunt yoke 33. The yoke 34 is a soft magnetic material having a substantially C shape or U shape. The yoke 34 is disposed in a manner to sandwich the permanent magnet 31 and shunt yoke 33. At a time of magnetic field ON, the permanent magnet 31 is vertically disposed, and the magnetic flux generated from the permanent magnet 31 is applied from the core 32 to the cartridge 100, and returns to the yoke 34 via the upper magnetic field generator (not shown). Specifically, the permanent magnet 31, core 32 and yoke 34 constitute a magnetic circuit. When the permanent magnet 31 is horizontally inclined, a closed loop is formed between the permanent magnet 31 and shunt yoke 33, and the magnetic field is turned off.

In order to compare the intensities of magnetic fields applied to the cartridge between the lower magnetic field generator of the standard apparatus and the lower magnetic field generator of the permanent magnet apparatus according to the embodiment, a probe of a teslameter was inserted at a position corresponding to the center of the sensing area of the cartridge, and the magnetic flux density was measured. The magnetic flux density of the standard apparatus was 14.2 mT at the time of lower magnetic field ON, and 0.0 mT at the time of magnetic field OFF. The magnetic flux density of the permanent magnet apparatus according to the embodiment was 42.0 mT at the time of lower magnetic field ON, and 0.0 mT at the time of magnetic field OFF. In this manner, compared to the standard apparatus in which the electromagnet is used as the lower magnetic field generator, the magnetic flux density is approximately tripled in the permanent magnet apparatus according to the embodiment.

In order to examine the difference in capability of attracting magnetic particles to the sensing area in the standard apparatus and the permanent magnet apparatus according to the embodiment, the following test was conducted. As a sample for the test, use was made of a sample in which an influenza A inactivated antigen was diluted in a buffer from a standard concentration to 1/16. A sample, in which magnetic particles that specifically bond to detection target molecule are added to this sample for the test, is injected in the cartridge, and is set in each of the standard apparatus and the permanent magnet apparatus. Thereafter, the lower magnetic field generators (the electromagnet in the standard apparatus, and the permanent magnet in the permanent magnet apparatus) were turned on for two minutes, and light signals of the light guide, which is coupled to the sensing area, were measured.

FIG. 7 is a graph illustrating time-based variations of light intensity signals relating to the standard apparatus and the permanent magnet apparatus according to the embodiment. The ordinate in FIG. 7 indicates the detected light intensity signals which are normalized with reference to t=0. It is indicated that, as the light intensity is lower, a greater number of magnetic particles adhere to the surface of the sensing area. In the standard apparatus, the light intensity decreases by about 20% with an elapsed time of two minutes. By contrast, in the permanent magnet apparatus, the light intensity sharply decreases by about 30% with an elapsed time of about 30 seconds. From this result, it is understood that in the permanent magnet apparatus, magnetic particles are attracted to the sensing area more quickly by stronger magnetic force. In the standard apparatus, the time that is needed to collect magnetic particles to the sensing area is about two minutes. On the other hand, in the permanent magnet apparatus, it is considered that about 30 seconds are sufficient.

Next, a description is given of a comparison between sample detection tests in the permanent magnet apparatus according to the embodiment and the standard apparatus. The sample detection tests are conducted in the following manner. After the cartridge is set, the light intensity, which is detected by the photodetector via the light guide, is monitored by the detection device, and, based on the degree of a decrease in light intensity, the magnetic particles existing in the evanescent region of the surface of the sensing area are analyzed/quantitatively determined. The detection tests of samples were conducted by using the permanent magnet apparatus according to the embodiment and the standard apparatus. As the sample, use was made of a sample in which predetermined detection target molecules (influenza A inactivated antigen) were diluted in a buffer. The concentrations of detection target molecules were set at three levels: 1/16 dilution of the standard concentration; 1/64 dilution; and no detection target molecule (blank).

The procedure of testing the sample is as follows. Step 1: a sample and magnetic particles are mixed, the mixture is injected in the cartridge, and the cartridge is set in each of the standard apparatus and the permanent magnet apparatus. Step 2: the lower magnetic field generator is turned on, and the magnetic particles are collected to the sensing area. Step 3: the lower magnetic field generator is turned off. Step 4: the upper magnetic field generator is turned on, and non-reacted magnetic particles are moved upward from the sensing area.

FIG. 8 is a graph illustrating reaction curves relating to samples of concentrations of three levels measured by the standard apparatus. In the standard apparatus, step 2 was conducted for two minutes, step 3 was conducted for five minutes, and step 4 was conducted for 30 seconds. After 450 seconds from the start of tests with the three concentrations of the blank, 1/64 dilution and 1/16 dilution, differences were recognized between the values of reaction curves in accordance with the concentrations of detection target molecules.

FIG. 9 is a graph illustrating reaction curves relating to samples of concentrations of three levels measured by the permanent magnet apparatus (sample analyzer) according to the embodiment. In the permanent magnet apparatus according to the embodiment, step 2 (ON of the lower magnetic field generator) was conducted for 30 seconds, step 3 was conducted for five minutes, and step 4 was conducted for 30 seconds. Despite the test time being shortened compared to the standard apparatus, clear differences are recognized between the three concentrations of the blank, 1/64 dilution and 1/16 dilution. After 360 seconds from the start of tests, the values of reaction curves differ in accordance with the concentrations of detection target molecules, and it is understood that the sensitivity performance of substantially the same level as with the standard apparatus is exhibited. From the above, it was confirmed that the test time can be shortened while the test sensitivity is maintained, by using the lower magnetic field generator according to the present embodiment.

As described above, the sample analyzer according to the embodiment includes at least the detection device 6, upper magnetic field generator 2 and lower magnetic field generator 3. The detection device 6 detects a target substance bonded to magnetic particles 220, the target substance and magnetic particles 220 being included in the sample 200 in the cartridge 100 and collected to the sensing area 120 in the cartridge 100. The upper magnetic field generator 2 applies a first magnetic field for releasing the magnetic particles 220, which are included in the sample 200, from the sensing area 120. The upper magnetic field generator 2 switches the application and shut-off of the first magnetic field. The lower magnetic field generator 3 includes the permanent magnet 31 configured to generate a second magnetic field for attracting the magnetic particles 220, which are included in the sample 200, to the sensing area 120; the core 32 configured to be excited by the permanent magnet 31; and the shunt yoke 33 configured to short-circuit the magnetic flux from the permanent magnet 31. The lower magnetic field generator 3 switches the application and shut-off of the second magnetic field by moving the permanent magnet 31 relative to the core 32 and shunt yoke 33.

By the above configuration, by moving the permanent magnet 31, the lower magnetic field generator 3 can subject the core 32 to magnetic seeding by the magnetic field from the permanent magnet 31, and can apply the magnetic field to the sample. In addition, by moving the permanent magnet 31, the lower magnetic field generator 3 can short-circuit the magnetic flux from the permanent magnet 31 by the shunt yoke 33, and can shut off the magnetic field to the sample from the permanent magnet 31. If the permanent magnet 31 moves when the magnetic field is switched from ON to OFF, the magnetic flux from the core 32 toward the cartridge 100 decreases, but the magnetic field distribution is hardly distorted. It is thus possible to suppress distortion of the distribution of the magnetic particles 220 on the sensing area 120. Specifically, even by the operation of switching the magnetic field from ON to OFF, the distribution of magnetic particles is not distorted, the density of the magnetic flux applied to the magnetic particles at the time of magnetic field OFF can be suppressed to be low, and the bond-reaction efficiency of magnetic particles to the sensing area 120 can be enhanced.

Additionally, by making the length in the longitudinal axis direction of the permanent magnet 31 greater than the width of the shunt yoke 33, almost all the magnetic flux generated from the permanent magnet 31 can be passed through the core 32. Thus, compared to the case in which the length in the longitudinal axis direction of the permanent magnet 31 is less than the width of the shunt yoke 33, the intensity of the magnetic field applied to the sample can be increased. Therefore, when the magnetic field is applied in order to collect the magnetic particles, the magnetic flux with high density can be applied to the sample and the magnetic particles can be collected quickly and efficiently.

Additionally, it is thinkable to substitute an electromagnet for the permanent magnet 31 according to the embodiment, as the magnet which can switch the ON/OFF of the magnetic field. When a magnetic flux density, which is equal to the magnetic flux density of the permanent magnet 31, is obtained by the electromagnet, it is necessary to increase the number of windings of the coil or to increase the electric current which is caused to flow in the coil. Accordingly, if a high magnetic flux density is to be obtained by the electromagnet, the dimensions of the magnetic field generator increase, and the power consumption becomes high, resulting in heat production. Thus, in the lower magnetic field generator 3 according to the embodiment, by using the permanent magnet 31 in place of the electromagnet, the dimensions of the entirety of the lower magnetic field generator 3 can be reduced, and the power consumption can be decreased. Therefore, a simple-type sample analyzer, which is compact and is low in power consumption, can be manufactured.

Thus, according to the present embodiment, a high-sensitivity quantitative analysis result can be obtained quickly with high precision. By extension, the analysis time, to be more specific, the ON time of the magnetic field by the lower magnetic field generator 3, can be shortened, and the throughput of the analysis can be improved.

Application Example 1

In the lower magnetic field generator 3, in the magnetic field ON, the permanent magnet 31 and core 32 strongly attract each other by magnetic force, and, in the magnetic field OFF, the permanent magnet 31 and shunt yoke 33 strongly attract each other by magnetic force. Thus, at a time of switching the magnetic field of the lower magnetic field generator 3 from ON to OFF, a resistive force occurs when the permanent magnet 31 is moved away from the core 32, and an attractive force occurs when the permanent magnet 31 approaches the shunt yoke 33. In addition, at a time of switching the magnetic field of the lower magnetic field generator 3 from OFF to ON, a resistive force occurs when the permanent magnet 31 is moved away from the shunt yoke 33, and an attractive force occurs when the permanent magnet 31 approaches the core 33. In this manner, when the permanent magnet 31 is moved between the core 32 and the shunt yoke 33, a resistive torque to this movement occurs. It is thus necessary to move the permanent magnet 31 with operation power which is greater than the resistive torque. This leads to an increase in size of the driving device which moves the permanent magnet 31, an increase in power consumption, and an increase in cost.

FIG. 10 is a view illustrating the configuration of a sample analyzer according to application example 1 of the embodiment. As illustrated in FIG. 10, the sample analyzer according to application example 1 includes a torque reducing magnetic circuit 10, in addition to the processing circuitry 1, upper magnetic field generator 2, lower magnetic field generator 3, support frame 4, magnetic field control circuitry 5, detection device 6, display circuitry 7, input circuitry 8, and storage circuitry 9. The torque reducing magnetic circuit 10 generates a torque for canceling a torque which occurs in accordance with the switching between the application and the shut-off of the magnetic field from the permanent magnet 31 included in the lower magnetic field generator 3. The torque reducing magnetic circuit 10 is a magnetic circuit provided in the lower magnetic field generator 3.

Figure 11B:
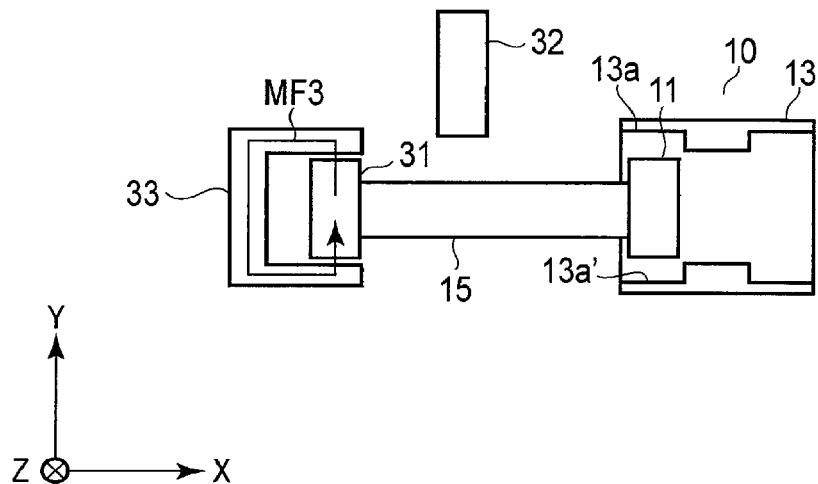
FIG. 11B is a view illustrating an arrangement in magnetic field OFF of the slide-type lower magnetic field generator and torque reducing magnetic circuit according to application example 1.
Figure 11C:
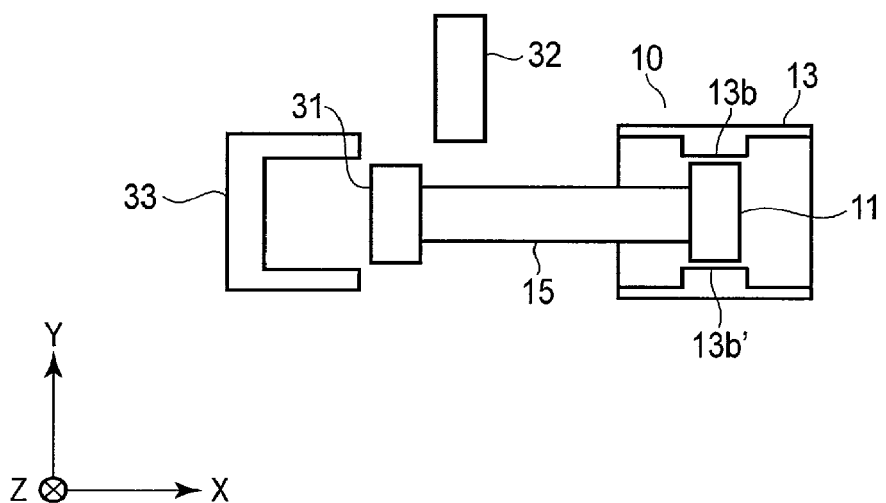
FIG. 11C is a view illustrating an arrangement in a state between between magnetic field ON and magnetic field OFF of the slide-type lower magnetic field generator and torque reducing magnetic circuit according to application example 1.

FIG. 11A, FIG. 11B and FIG. 11C are cross-sectional views illustrating a detailed arrangement of the lower magnetic field generator 3 of the type in which the permanent magnet 31 is slid, and the torque reducing magnetic circuit 10. FIG. 11A is a cross-sectional view illustrating a detailed arrangement in magnetic field ON of the lower magnetic field generator 3 and torque reducing magnetic circuit 10. FIG. 11B is a cross-sectional view illustrating a detailed arrangement in magnetic field OFF of the lower magnetic field generator 3 and torque reducing magnetic circuit 10. FIG. 11C is a cross-sectional view illustrating a detailed arrangement of the lower magnetic field generator 3 and torque reducing magnetic circuit 10 in a state between magnetic field ON and magnetic field OFF. As illustrated in FIG. 11A, FIG. 11B and FIG. 11C, the torque reducing magnetic circuit 10 includes a permanent magnet 11 and a yoke 13 (third soft magnetic material). The permanent magnet 11 has substantially the same shape as the permanent magnet 31. The yoke 13 confines the magnetic flux, which is generated by the permanent magnet 11, within the yoke 13, thereby suppressing the influence on the magnetic field which is applied from the lower magnetic field generator 3 to the cartridge 100. The yoke 13 is a soft magnetic material having a C shape, a U shape or an annular shape, so as to be able to surround the permanent magnet 11.

FIG. 12A, FIG. 12B, FIG. 12C, FIG. 12D and FIG. 12E are views illustrating a detailed configuration of the torque reducing magnetic circuit 10 provided in the lower magnetic field generator 3 of the type in which the permanent magnet 11 is slid. FIG. 12A is a perspective view of the torque reducing magnetic circuit 10 including a yoke 13 having a C shape or a U shape. FIG. 12B is a perspective view of the torque reducing magnetic circuit 10 including a yoke 13 having an annular shape. FIG. 12C is a view showing an AA' cross-section of FIG. 12A. FIG. 12D is a view showing an AA' cross-section of FIG. 12B. FIG. 12E is a view showing a BB' cross-section of FIG. 12A and FIG. 12B. As illustrated in FIG. 12A, FIG. 12B, FIG. 12C, FIG. 12D and FIG. 12E. The yoke 13 has inner surfaces 13$a$, 13$a'$, 13$b$, 13$b'$, 13$c$ and 13$c'$, which are opposed to the magnetic poles of the permanent magnet 11. The inner surfaces of the yoke 13 are processed and formed with steps, such that a distance between the inner surfaces 13$b$ and 13$b'$ becomes narrower than a distance between the inner surfaces 13$a$ and 13$a'$ and a distance between the inner surfaces 13$c$ and 13$c'$. When the permanent magnet 11 is positioned to be opposed to the inner surfaces 13$b$ and 13$b'$, the distance between the permanent magnet 11 and inner surfaces 13$b$ and 13$b'$ is small. When the permanent magnet 11 is positioned to be opposed to the inner surfaces 13$a$ and 13$a'$ or the inner surfaces 13$c$ and 13$c'$, the distance between the permanent magnet 11 and the inner surfaces 13$a$ and 13$a'$ or inner surfaces 13$c$ and 13$c'$ is large.

The permanent magnet 11 is mechanically fixed to the permanent magnet 31 via a nonmagnetic connection arm 15. Since the permanent magnet 11 is fixed to the permanent magnet 31 via the connection arm 15, the permanent magnet 11 moves in interlock with the permanent magnet 31, and slides within the space (opening) surrounded by the C shape, U shape or annular shape of the yoke 13. In the state in which the permanent magnet 31 is in close proximity to the core 32 (magnetic field ON), the permanent magnet 11 is disposed to be opposed to the inner surfaces 13$c$ and 13$c'$ of the yoke 13 (FIG. 11A). In the state in which the permanent magnet 31 is in close proximity to the shunt yoke (magnetic field OFF), the permanent magnet 11 is disposed to be opposed to the inner surfaces 13$a$ and 13$a'$ of the yoke 13 (FIG. 11B). When the permanent magnet 31 is at an intermediate position between the core 32 and shunt yoke 33, the permanent magnet 11 is disposed to be opposed to the inner surfaces 13$b$ and 13$b'$ of the yoke 13 (FIG. 11C). By this disposition, the resistive force at a time when the permanent magnet 31 is moved away from the core 32 is canceled by the attractive force between the permanent magnet 11 and yoke 13, and the resistive force at a time when the permanent magnet 31 is moved away from the shunt yoke 33 is canceled by the attractive force between the permanent magnet 11 and yoke 13. Thereby, the ON/OFF switching operation of the magnetic field by the lower magnetic field generator 3 can be performed with a small moving force.

By the configuration of the yoke 13 of the torque reducing magnetic circuit 10 as illustrated in FIG. 12A, FIG. 12B, FIG. 12C, FIG. 12D and FIG. 12E, even if the permanent magnet 11 slides by the magnetic field switching operation, the permanent magnet 11 stays within the opening of the yoke 13 (the space surrounded by the yoke 13), and thus the magnetic flux generated by the permanent magnet 11 is shut off by the yoke 13. In addition, the permanent magnet 11 and yoke 13, which constitute the torque reducing magnetic circuit 10, may preferably be disposed at a predetermined distance or more from the core 32, permanent magnet 31 and shunt yoke 33. By this disposition, it is possible to reduce the influence which is exerted by the magnetic flux generated from the permanent magnet 11 upon the magnetic field which is applied to the cartridge 100.

It should suffice if the shapes of the inner surfaces 13$a$, 13$a'$, 13$b$, 13$b'$, 13$c$ and 13$c'$ of the yoke 13, which are opposed to the permanent magnet 11, satisfy the above-described conditions. These shapes are not limited to those illustrated in FIG. 12A, FIG. 12B, FIG. 12C, FIG. 12D and FIG. 12E. It should suffice if the permanent magnet 31 and permanent magnet 11 have a positional relationship in which the permanent magnet 31 and permanent magnet 11 are spaced apart by such a predetermined distance that the mutual influences of the magnetic fields generated by the permanent magnet 31 and permanent magnet 11 are ignorable. For example, the permanent magnet 11 and permanent magnet 31 may have different directions of magnetization. However, the permanent magnet 11 and permanent magnet 31 may preferably be disposed to have the magnetic poles in the same direction, in order to prevent the magnetic flux from the N pole of one of the permanent magnet 11 and permanent magnet 31 from flowing to the S pole of the other. In the meantime, FIG. 11A, FIG. 11B, FIG. 11C, FIG. 12A, FIG. 12B, FIG. 12C, FIG. 12D and FIG. 12E merely illustrate the structural components of the magnetic circuit and their arrangement. Actually, a jig for fixing the respective components, a moving mechanism, etc. may be included.

FIG. 13A, FIG. 13B and FIG. 13C are views illustrating a detailed arrangement of the lower magnetic field generator 3 of the type in which the permanent magnet 31 is rotated, and the torque reducing magnetic circuit 10. FIG. 13A is a view illustrating a detailed arrangement in magnetic field ON of the lower magnetic field generator 3 and torque reducing magnetic circuit 10. FIG. 13B is a view illustrating a detailed arrangement in magnetic field OFF of the lower magnetic field generator 3 and torque reducing magnetic circuit 10. FIG. 13C is a view illustrating a detailed arrangement of the lower magnetic field generator 3 and torque reducing magnetic circuit 10 in a state between magnetic field ON and magnetic field OFF. As illustrated in FIG. 13A, FIG. 13B and FIG. 13C, the permanent magnet 31 of the lower magnetic field generator 3 and the permanent magnet 11 of the torque reducing magnetic circuit 10 are disposed such that the rotational axis RR1 of the permanent magnet 31 and a rotational axis RR2 of the permanent magnet 11 are disposed coaxial. The permanent magnet 31 of the lower magnetic field generator 3 and the permanent magnet 11 of the torque reducing magnetic circuit 10 are mechanically connected to a connection arm 230 (not shown) so as to rotate in the same direction at the same time. For example, the permanent magnet 11 and permanent magnet 31 may preferably be connected to the connection arm 230 so as to keep the same angle in a direction about the rotational axis RR1, RR2. The connection arm 230 may preferably be formed of a nonmagnetic material in order to prevent disturbance of the magnetic field from the permanent magnet 11.

The yoke 13 is a soft magnetic material having such an annular shape as to be able to surround the permanent magnet 11. The yoke 13 is disposed such that the center axis of the annular shape thereof matches with the rotational axis RR2. The yoke 13 confines the magnetic flux, which is generated by the permanent magnet 11, within the yoke 13, thereby suppressing the influence on the magnetic field which is applied from the lower magnetic field generator 3 to the cartridge 100. The diameter of the opening of the yoke 13 has different lengths in accordance with the angle about the center axis (rotational axis RR2), so that a distance D13 between a magnetic pole surface 11a, 11b of the permanent magnet 11 and a surface 13a of the yoke 13 may vary in accordance with the rotation of the permanent magnet 11 about the rotational axis RR2. Specifically, the surface 13a of the yoke 13 is processed in such a shape that the distance D13 becomes maximum in the state in which the permanent magnet 31 is in close proximity to the core 32, that is, in the state in which the magnetic field of the lower magnetic field generator 3 is turned on (FIG. 13A), and in the state in which the permanent magnet 31 is in close proximity to the shunt yoke 33, that is, in the state in which the magnetic field of the lower magnetic field generator 3 is turned off (FIG. 13B), and that the distance D13 becomes minimum in the state in which the permanent magnet 31 is neither in close proximity to the core 32 nor in close proximity to the shunt yoke 33, that is, in a midway state of switching between ON and OFF of the magnetic field (FIG. 13C).

It should suffice if the shape of the surface 13a of the yoke 13, which is opposed to the permanent magnet 11, satisfies the above conditions. The shape of the surface 13a is not limited to that illustrated in FIG. 13A and FIG. 13B. In addition, it should suffice if the permanent magnet 31 and permanent magnet 11 have a positional relationship in which the permanent magnet 31 and permanent magnet 11 are spaced apart by such a predetermined distance that the mutual influences of the magnetic fields generated by the permanent magnet 31 and permanent magnet 11 are ignorable. For example, the permanent magnet 11 and permanent magnet 31 may be kept at different angles about the rotational axes RR1 and RR2. However, the permanent magnet 11 and permanent magnet 31 may preferably be disposed to have the magnetic poles in the same direction, in order to prevent the magnetic flux from the N pole of one of the permanent magnet 11 and permanent magnet 31 from flowing to the S pole of the other. In the meantime, FIG. 13A, FIG. 13B and FIG. 13C merely illustrate the structural components of the magnetic circuit and their arrangement. Actually, a jig for fixing the respective components, a connection arm 230 and a moving mechanism for coupling the permanent magnet 31 and permanent magnet 11 and rotating them at the same time about the rotational axis RR1, etc. may be included.

Next, the torque reducing effect by the torque reducing magnetic circuit 10 is described. Torque reducing effects are compared between the lower magnetic field generator 3 without the torque reducing magnetic circuit 10 and the lower magnetic field generator 3 with the torque reducing magnetic circuit 10. FIG. 14A illustrates the configuration of the lower magnetic field generator 3 without the torque reducing magnetic circuit 10. FIG. 14B illustrates the configuration of the lower magnetic field generator 3 with the torque reducing magnetic circuit 10. Incidentally, FIG. 14A and FIG. 14B illustrate the arrangement of magnetic materials which constitute the magnetic circuit, and, actually, nonmagnetic components for fixing respective magnetic material components are added. In the lower magnetic field generator 3 with the torque reducing magnetic circuit 10 illustrated in FIG. 14B, the permanent magnet 31 and permanent magnet 11 are mechanically fixed by the nonmagnetic connection arm 230 which is not illustrated in FIG. 14B. Thus, the permanent magnet 31 and permanent magnet 11 rotate in the same direction at the same time.

FIG. 15 is a graph illustrating variations of torque due to the rotation of the permanent magnets 31 in the magnetic circuits of FIG. 14A and FIG. 14B. In FIG. 15, the state in which the permanent magnet 31 is in the vertical direction (magnetic field ON) corresponds to a rotational angle 0°, and the state in which the permanent magnet 31 is in the horizontal direction (magnetic field OFF) corresponds to a rotational angle 90°. When the magnetic field is switched from ON to OFF (rotational angle 0°→90°), the value of torque in the negative direction becomes a resistive force. When the magnetic field is switched from OFF to ON (rotational angle 90°→0°, the value of torque in the positive direction becomes a resistive force. Compared to the lower magnetic field generator 3 without the torque reducing magnetic circuit 10 (FIG. 14A), in the lower magnetic field generator 3 with the torque reducing magnetic circuit 10 (FIG. 14B), the torque decreases remarkably, and only a small driving force is needed for the ON/OFF switching of the magnetic field. Therefore, in the sample analyzer according to the embodiment, the permanent magnet 31 can be operated by a small-sized, inexpensive moving mechanism.

Application Example 2

In the above-described embodiment, the lower magnetic field generator 3 was described as being equipped with a single torque reducing magnetic circuit 10. However, the embodiment is not limited to this. In a lower magnetic field generator 3 according to application example 2, two torque reducing magnetic circuits, namely a torque reducing magnetic circuit 11 and a torque reducing magnetic circuit 11', are provided. In the description below, the structural elements having substantially the same functions as in the above-described embodiment are denoted by like reference numerals, and an overlapping description will be given only where necessary.

FIG. 16 is a view illustrating the configuration of a sample analyzer according to application example 2. As illustrated in FIG. 16, the sample analyzer according to application example 2 includes a torque reducing magnetic circuit 11 and a torque reducing magnetic circuit 11', in addition to the processing circuitry 1, upper magnetic field generator 2, lower magnetic field generator 3, support frame 4, magnetic field control circuitry 5, detection device 6, display circuitry 7, input circuitry 8, and storage circuitry 9. The torque reducing magnetic circuits 11 and 11' generate torques for canceling a torque which occurs in accordance with the switching between the application and the shut-off of the magnetic field from the permanent magnet 31 included in the lower magnetic field generator 3. The torque reducing magnetic circuits 11 and 11' are magnetic circuits provided in the lower magnetic field generator 3.

Figure 18:
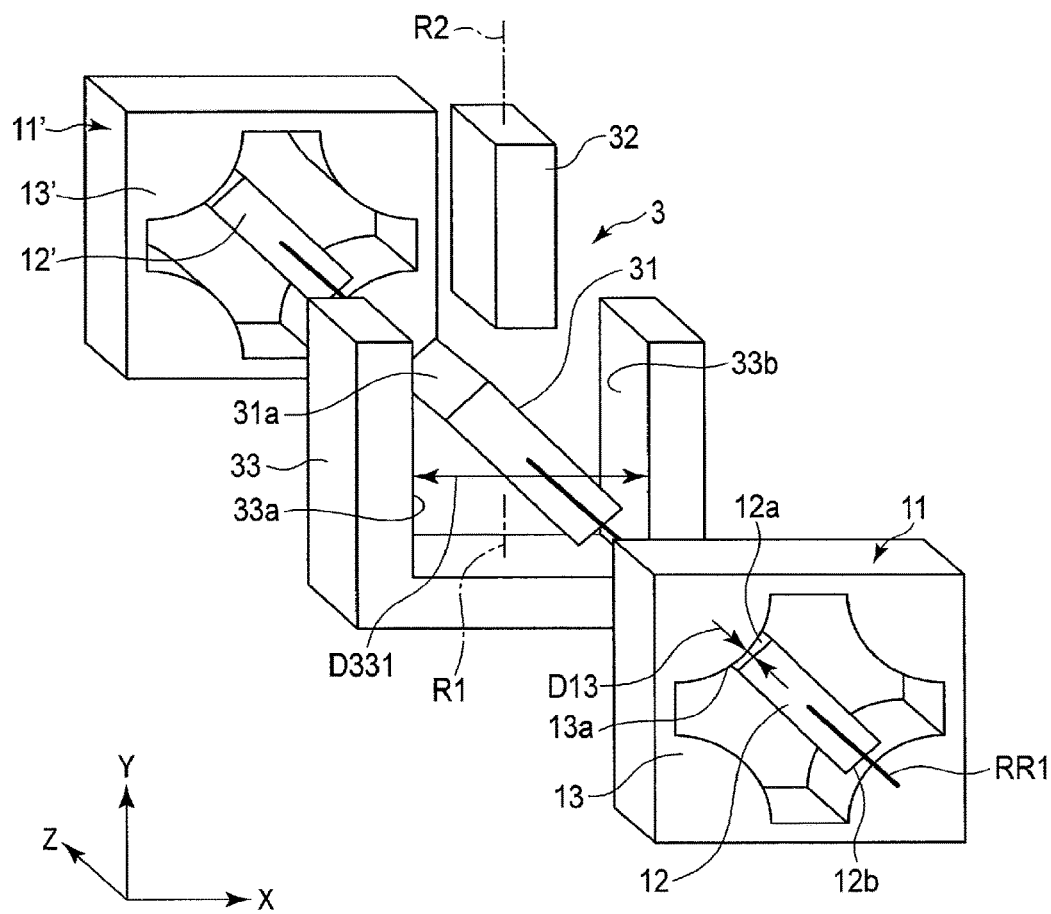
FIG. 18 is a perspective view illustrating an arrangement of the lower magnetic field generator, the torque reducing magnetic circuit and the other torque reducing magnetic circuit.

FIG. 17 is a view illustrating an arrangement of the cartridge 100, upper magnetic field generator 2, lower magnetic field generator 3, torque reducing magnetic circuit 11 and torque reducing magnetic circuit 11' according to application example 2. FIG. 18 is a perspective view illustrating an arrangement of the lower magnetic field generator 3, torque reducing magnetic circuit 11 and torque reducing magnetic circuit 11'. The structural elements, other than the torque reducing magnetic circuit 11 and torque reducing magnetic circuit 11', which are illustrated in FIG. 17 and FIG. 18, are substantially identical to the structural elements illustrated in FIG. 2. In addition, the configuration of each of the torque reducing magnetic circuit 11 and torque reducing magnetic circuit 11', which are illustrated in FIG. 17 and FIG. 18, is the same as the configuration of the torque reducing magnetic circuit 10 according to application example 1.

As illustrated in FIG. 17 and FIG. 18, the torque reducing magnetic circuit 11 includes an annular yoke 13 and a permanent magnet 12, and the torque reducing magnetic circuit 11' includes an annular yoke 13' and a permanent magnet 12'. The material of the permanent magnets 12 and 12' may be selected in consideration of cost, etc., in accordance with the material of the permanent magnet 31, in order to cancel the torque which is generated by the lower magnetic field generator 3. For example, as the permanent magnet 12, 12', any kind of existing permanent magnets may be used, such as a ferrite magnet, an alnico magnet, a samarium-cobalt magnet, or a neodymium magnet. The permanent magnets 12 and 12' are mechanically fixed to the permanent magnet 31 by a member having nonmagnetic material quality, and are configured to be rotatable about the rotational axis RR1 together with the permanent magnet 31. The annular yoke 13 is a soft magnetic material surrounding the permanent magnet 12, and is disposed such that the center axis of the annular shape thereof matches with the rotational axis RR1 of the permanent magnet 12. Similarly, the annular yoke 13' is a soft magnetic material surrounding the permanent magnet 12', and is disposed such that the center axis of the annular shape thereof matches with the rotational axis RR1 of the permanent magnet 12'.

As illustrated in FIG. 18, the transverse width of the permanent magnet 12, 12' is set to be substantially equal to or less than the transverse width of the annular yoke 13, 13'. By this dimension, the annular yoke 13, 13' can confine the magnetic flux, which is generated by the permanent magnet 12, 12', within the annular yoke 13, 13'. Accordingly, it is possible to suppress the influence which the torque reducing magnetic circuit 11, 11' exerts upon the magnetic field which is applied from the lower magnetic field generator 3 to the cartridge 100. As the material of the shunt yoke 33, core 32 and annular yokes 13 and 13', use may be made of a material such as rolled steel for general structures, which is inexpensive, is easily available, and has relatively uniform magnetic characteristics.

As illustrated in FIG. 18, the diameter of the opening of the annular yoke 13, which constitutes the torque reducing magnetic circuit 11, has different lengths in accordance with the angle about the rotational axis RR1, so that the distance D13 between the magnetic pole surface 12a, 12b of the permanent magnet 12 and the inner surface 13a may vary in accordance with the rotation of the permanent magnet 12 about the rotational axis RR1. Specifically, the inner surface 13a of the annular yoke 13, 13' is formed such that the distance D13 becomes maximum in the state in which the permanent magnet 31 is in close proximity to the core 32, that is, in the state in which the magnetic field of the lower magnetic field generator 3 is turned on (e.g. FIG. 5C), and in the state in which the permanent magnet 31 is in close proximity to the shunt yoke 33, that is, in the state in which the magnetic field of the lower magnetic field generator 3 is turned off (e.g. FIG. 5D). In addition, the inner surface 13a of the annular yoke 13, 13' is formed such that the distance D13 becomes minimum in the state in which the permanent magnet 31 is neither in close proximity to the core 32 nor in close proximity to the shunt yoke 33, that is, in a midway state of switching between ON and OFF of the magnetic field (e.g. FIG. 18). It should suffice if the shape of the surface 13a of the annular yoke 13, which is opposed to the permanent magnet 12, satisfies the above conditions. The shape of the surface 13a is not limited to that illustrated in FIG. 18. The shape of the annular yoke 13' of the torque reducing magnetic circuit 11', and the relationship between the magnetic poles of the permanent magnet 12' and the diameter of the opening of the annular yoke 13' are the same as in the case of the torque reducing magnetic circuit 11.

The permanent magnet 31 and permanent magnet 12, and the permanent magnet 31 and permanent magnet 12'; are disposed to be spaced apart by such a predetermined distance that the mutual influences of the magnetic fields generated by these permanent magnets are ignorable. The permanent magnet 12, 12' and permanent magnet 31 may be kept at mutually different rotational angles about the rotational axis RR1. However, the permanent magnet 12, 12' and permanent magnet 31 may preferably be disposed to have the magnetic poles in the same direction, in order to prevent the magnetic flux from the N pole of one of the permanent magnet 12, 12' and permanent magnet 31 from flowing to the S pole of the other.

In the meantime, FIG. 18 merely illustrates the structural components of the magnetic circuit and their arrangement. Actually, a jig for fixing the respective components, a connection arm and a moving mechanism for coupling the permanent magnet 31 and permanent magnet 12, 12' and rotating them at the same time about the rotational axis RR1, etc. may be included. For example, as illustrated in FIG. 19, the lower magnetic field generator 3, torque reducing magnetic circuit 11 and torque reducing magnetic circuit 11' are accommodated in a housing 60. The housing 60 is formed of a member with nonmagnetic material quality, such as brass or aluminum. The housing 60 supports the permanent magnet 31 of the lower magnetic field generator 3, the permanent magnet 12 of the torque reducing magnetic circuit 11 and the permanent magnet 12' of the torque reducing magnetic circuit 11' such that these permanent magnets are rotatable as one piece about the rotational axis RR1.

The two torque reducing magnetic circuits 11 and 11', as illustrated in FIG. 18, are disposed to be opposed to each other, with the lower magnetic field generator 3 being interposed. By this disposition, the torque, which occurs at the center of the lower magnetic field generator 3, is canceled, on the left and right sides, by the torques occurring at the torque reducing magnetic circuits 11 and 11' on both sides of the center of the lower magnetic field generator 3, and the occurrence of a twist can be decreased.

Furthermore, the lower magnetic field generator 3 has such a geometry that the permanent magnet 31, core 32 and shunt yoke 33 are symmetric with respect to an imaginary cross-section S (shown in FIG. 17) which extends through the center of the lower magnetic field generator 3 and is perpendicular to the rotational axis RR1. In addition, the two torque reducing magnetic circuits 11 and 11' have substantially the same configuration, and are disposed equidistant from the plane S, with the lower magnetic field generator 3 being interposed. Thereby, the lower magnetic field generator 3, as a whole, forms a magnetic circuit which is symmetric with respect to the plane S. Additionally, the lower magnetic field generator 3 is disposed relative to the cartridge 100 such that the center axis of the core 32 matches with the center of the sample 200 and sensing area 120. By configuring and disposing the lower magnetic field generator 3 in this manner, the torque occurring at the permanent magnet 31 at the center of the lower magnetic field generator 3 is canceled by the torques occurring at the torque reducing magnetic circuits 11 and 11' on both sides of the lower magnetic field generator 3. Since the torques occurring at the two torque reducing magnetic circuits 11 and 11' are equal, a twist due to a decrease in torque does not occur. Additionally, at this time, since the magnetic circuit of the lower magnetic field generator 3 is, as a whole, symmetric with respect to the plane S, the magnetic field distribution, which is formed in the sample 200 and on the sensing area 120 when the magnetic field of the lower magnetic field generator 3 is turned on, becomes symmetric. As a result, a deviation of the distribution of magnetic particles, which are collected by the sensing area by the magnetic field, is reduced, and the particles are distributed more uniformly. Therefore, bond-reactions of the magnetic particles with the surface of the sensing area 120 can be caused efficiently, and the test sensitivity can be enhanced.

Application Example 3

In a sample analyzer according to application example 3, the inner surface 33a of the shunt yoke 33, which is opposed to the magnetic pole 31b of the permanent magnet 31, is formed such that the distance between the magnetic pole 31b of the permanent magnet 31 of the lower magnetic field generator 3, which is opposed to the shunt yoke 33, and the inner surface 33a of the shunt yoke 33, which is opposed to the magnetic pole 31b of the permanent magnet 31, is kept substantially constant, even when the permanent magnet 31 rotates about the rotational axis RR1. Hereinafter, the sample analyzer according to application example 3 is described in detail. In the description below, the structural elements having substantially the same functions as in the above-described embodiment are denoted by like reference numerals, and an overlapping description will be given only where necessary.

FIG. 20A and FIG. 20B are views showing that the torque of the permanent magnet 31 varies depending on the shape of the inner surface of the shunt yoke 33 of the lower magnetic field generator 3. FIG. 20A and FIG. 20B are cross-sectional views each illustrating a midway state of switching from magnetic field ON to magnetic field OFF, with the permanent magnet 31 rotating clockwise. The shunt yoke 33 in FIG. 20A has a U shape which is bent substantially at right angles. In this case, the distance between the magnetic pole 31a, 31b of the permanent magnet 31, which is opposed to the shunt yoke 33, and the inner surface 33a of the shunt yoke 33, which is opposed to the magnetic pole 31a, 31b of the permanent magnet 31, varies in accordance with the rotation of the permanent magnet 31 about the rotational axis RR1. Accordingly, during the period in which the magnetic field ON is being switched to the magnetic field OFF, the magnetic pole 31a of the permanent magnet 31 moves away from the magnet facing surface 32b of the core 32, and the magnet pole 31b moves away from that inner surface 33a of the shunt yoke 33, which faces the permanent magnet 31. Thus, as illustrated in FIG. 20A, magnetic resistive forces t1 and t2 in a direction opposite to the rotational direction act at two locations, i.e. the magnetic poles 31a and 31b. Thus, in order to switch the magnetic field by rotating the permanent magnet 31, a large torque, which is stronger than the resistive force t1, t2, is required.

On the other hand, as illustrated in FIG. 20B, the inner surface 33a of the shunt yoke 33 according to application example 3 has such a shape that the distance between the magnet pole 31b of the permanent magnet 31 and the inner surface 33a is substantially invariable, regardless of the rotation of the permanent magnet 31. To be more specific, that part of the inner surface 33a, which is located below the rotational axis RR1, is formed in a semicircular shape having the center at the rotational axis RR1. By virtue of this shape, even if the permanent magnet 31 rotates about the rotational axis RR1, the direction of the magnetic flux, which acts between the magnet pole 31b of the permanent magnet 31 and the shunt yoke 33, is kept perpendicular to the rotational direction of the permanent magnet 31, and therefore no resistive force to rotation occurs. Thus, in the case of FIG. 20B, since only the attractive force between the magnet pole 31a of the permanent magnet 31 and the core 32, as indicated by t1, contributes to the torque, the torque is halved compared to the case of FIG. 20A.

If the torque occurring in the lower magnetic field generator 3 can be reduced, as in application example 3, the torque reducing magnetic circuit 11 and torque reducing magnetic circuit 11' can be reduced in size accordingly, and furthermore the driving device for rotating the permanent magnets 31, 12 and 12' can be reduced in size. Therefore, the size of the entirety of the sample analyzer according to the embodiment can be reduced, and the manufacturing cost and power consumption can be reduced. Thereby, it becomes possible to realize a small-sized sample analyzer, which enables easy switching driving of the ON/OFF of the magnetic field.

Application Example 4

In a sample analyzer according to application example 4, the shunt yoke 33 is magnetically connected to at least one of the annular yoke 13 of the torque reducing magnetic circuit 11 and the annular yoke 13' of the torque reducing magnetic circuit 11'. Hereinafter, the sample analyzer according to application example 4 is described in detail. In the description below, the structural elements having substantially the same functions as in the above-described embodiment are denoted by like reference numerals, and an overlapping description will be given only where necessary.

Figure 21C:
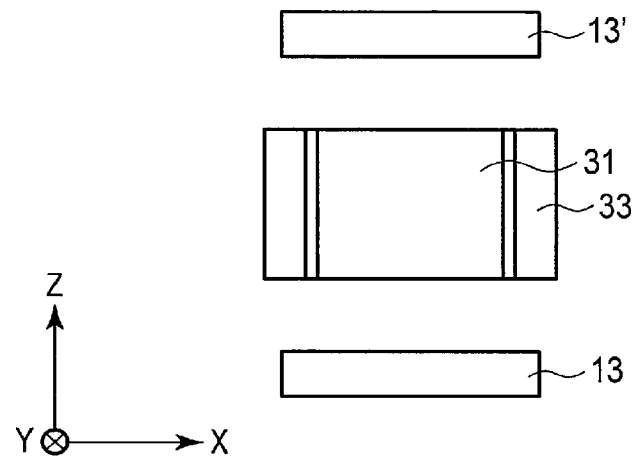
FIG. 21C is a plan view of FIG. 21B.

FIG. 21A is a perspective view of the lower magnetic field generator 3, torque reducing magnetic circuit 11 and torque reducing magnetic circuit 11', in such a configuration that the shunt yoke 33 and annular yokes 13 and 13' are not magnetically connected. FIG. 21B is a view illustrating a magnetic flux in an overlapping manner on a transverse cross-sectional view of FIG. 21A at a time of magnetic field OFF. FIG. 21C is a plan view of FIG. 21B.

As illustrated in FIG. 21B, at the time of magnetic field OFF, the permanent magnet 31 is disposed horizontal, and such a closed loop is formed that most of the magnetic flux MF1, which is generated from one magnetic pole of the permanent magnet 31, passes through the shunt yoke and returns to the other opposite-side magnetic pole of the permanent magnet 31. However, a very small portion of the magnetic flux MF1, which is generated from one magnetic pole of the permanent magnet 31, leaks from terminal ends of the shunt yoke 33 and core 32, and becomes a leak magnetic field to the cartridge 100. This leak magnetic field imparts slight magnetization, even in the state of magnetic field OFF, to the magnetic particles 220 collected to the sensing area 120 by magnetic field ON. As a result, magnetic force acts on the magnetic particles 220, or agglomeration of the magnetic particles 220 is promoted. Thus, the thermal motion of the magnetic particles 220 is hindered, leading to a factor of hindrance of bond-reactions of the magnetic particles 220 with the sensing area 120. In order to reduce the leak magnetic field, there is a method of changing the material of the shunt yoke 33 to a material with high magnetic permeability, or enlarging the shunt yoke 33 and substantially increasing the cross section through which the magnetic flux passes. However, the material with high magnetic permeability is generally expensive, and if the shunt yoke 33 is too large, the apparatus as a whole increases in size and weight, leading to an increase in cost.

Figure 22A:
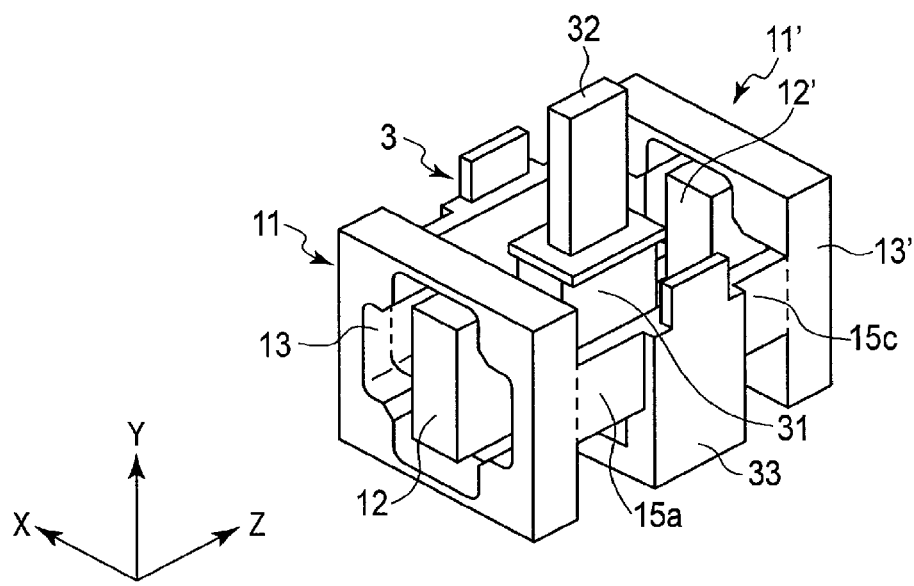
FIG. 22A is a perspective view of a lower magnetic field generator, a torque reducing magnetic circuit and another torque reducing magnetic circuit, which are magnetically connected, according to application example 4.

FIG. 22A is a perspective view of the lower magnetic field generator 3, torque reducing magnetic circuit 11 and torque reducing magnetic circuit 11', in such a configuration that the shunt yoke 33 and annular yokes 13 and 13' are magnetically connected. FIG. 22B is a view illustrating a magnetic flux in an overlapping manner on a transverse cross-sectional view of FIG. 22A at a time of magnetic field OFF. FIG. 22C is a plan view of FIG. 22B.

As illustrated in FIG. 22A, FIG. 22B and FIG. 22C, the shunt yoke 33 and annular yoke 13 are magnetically connected by connection yokes 15a and 15b, and the shunt yoke 33 and annular yoke 13' are magnetically connected by connection yokes 15c and 15d. Here, "magnetically connected" means a state in which, for example, the shunt yoke 33 and connection yoke 15a, and the connection yoke 15a and annular yoke 13, are put in physical contact or disposed in very close proximity, and the magnetic flux easily passes from the shunt yoke 33 to the annular yoke 13 via the connection yoke 15a. The material of the connection yokes 15a, 15b, 15c and 15d may be the same soft magnetic material as the material of the shunt yoke 33 and annular yokes 13 and 13'. Besides, each of the connection yokes 15a, 15b, 15c and 15d may be an independent soft magnetic material component, or may be a part of the integral structure with the shunt yoke 33 or annular yoke 13, 13'.

As illustrated in FIG. 22B and FIG. 22C, at the time of magnetic field OFF, the magnetic flux, which is generated from the permanent magnet 31, forms not only a closed loop MF1 in which the magnetic flux passes through the inside of the shunt yoke 33 and returns to the permanent magnet 31, but also a closed loop MF2 in which the magnetic flux passes through the connection yoke 15a, annular yoke 13 and connection yoke 15b and returns to the permanent magnet 31, and a closed loop MF3 in which the magnetic flux passes through the connection yoke 15c, annular yoke 13' and connection yoke 15d and returns to the permanent magnet 31. In this manner, since the sample analyzer according to application example 4 includes a greater number of paths for confining the magnetic flux generated from the permanent magnet 31 at the time of magnetic field OFF, the leak magnetic field is small, compared to the sample analyzer with no connection yoke as illustrated in FIG. 21A, FIG. 21B and FIG. 21C.

A description is given of the ON/OFF switching operation of the magnetic field by the above-described lower magnetic field generator 3. When the magnetic field is turned on, the magnetic field control circuitry 5 supplies an ON signal to the driving device (not shown) in the lower magnetic field generator 3. As illustrated in FIG. 18, the driving device rotates the permanent magnet 31 about the rotational axis RR1, and approaches the magnetic pole surface 31a or 31b to the bottom surface 32b of the core 32. In other words, the longitudinal axis R1 of the permanent magnet 31 is made to agree with the longitudinal axis R2 of the core 32. At this time, the magnetic flux MF3, which is generated from the permanent magnet 31, passes through the core 32, and is applied to the sample 200 stored in the cartridge 100 that is located on the opposite side of the core 32.

When the magnetic field is turned off, the magnetic field control circuitry 5 supplies a magnetic field shut-off signal to the driving device (not shown) in the lower magnetic field generator 3. As illustrated in FIG. 18, the driving device rotates the permanent magnet 31 about the rotational axis RR1, and approaches the magnetic pole surfaces 31a and 31b to the shunt yoke 33. To be more specific, the driving device makes the longitudinal axis R1 of the permanent magnet 31 perpendicular to the longitudinal axis R2 of the core 32. By this rotation, the magnetic poles 31a and 31b are opposed to the inner surfaces of the shunt yoke 33. At this time, the magnetic flux MF3, which is generated from the permanent magnet 31, forms such a closed loop that the magnetic flux MF3 passes through the shunt yoke 33 and returns to the permanent magnet 31. Thus, most of the magnetic flux is not guided to the core 32, and the magnetic field, which is applied to the inside of the cartridge 100, is substantially shut off.

In both the case of turning on the magnetic field and the case of turning off the magnetic field, the permanent magnets 12 and 12' included in the torque reducing magnetic circuits 11 and 11' rotate about the rotational axis RR1 in the same direction as one piece with the permanent magnet 31, as illustrated in FIG. 18, and generates the torque for reducing the resistive torque occurring in the lower magnetic field generator 3.

In the meantime, FIG. 21A, FIG. 21B, FIG. 21C, FIG. 22A, FIG. 22B and FIG. 22C illustrate the arrangement of magnetic material components which are minimum necessary components of the magnetic circuit of the lower magnetic field generator 3. Actually, the core 32, shunt yoke 33, annular yokes 13 and 13' and connection yokes 15a, 15b, 15c and 15d are fixed to each other as magnetic material components, or are mechanically fixed in the unit, by a nonmagnetic structure. In addition, the permanent magnets 31, 12 and 12' are fixed by a nonmagnetic structure and constitute an integral rotary body. This rotary body is disposed in a limited space by bearings, etc., so that the rotary body may rotate about the rotational axis RR1 in the annular yokes 13 and 13' and shunt yoke 33. Furthermore, this rotary body is connected to the driving device, and rotates under the control of the magnetic field control circuitry 5, and thereby the ON/OFF of the magnetic field can be switched.

Application Example 5

In the above-described embodiment, the magnetic field control circuitry 5 is configured to alternately apply the magnetic field from the upper magnetic field generator 2 and the magnetic field from the lower magnetic field generator 3 to the sample. However, the embodiment is not limited to this. A magnetic field control circuitry 5 according to application example 5 is configured to be able to apply, at the same time, the magnetic field from the upper magnetic field generator 2 and the magnetic field from the lower magnetic field generator 3 to the sample.

FIG. 23 is a view illustrating the configuration of a sample analyzer according to application example 5. As illustrated in FIG. 23, when the magnetic field control circuitry 5 turns on the magnetic field of the lower magnetic field generator 3, the magnetic field control circuitry 5 controls the upper magnetic field generator 2 and the lower magnetic field generator 3 so as to turn on the magnetic field of the upper magnetic field generator 2 at the same time. As a result, a composite magnetic field of the magnetic field generated from the lower magnetic field generator 3 and the magnetic field generated from the upper magnetic field generator 2 is applied to the sample 200.

FIG. 24 is a view illustrating the configuration of the sample analyzer, and illustrating in detail the arrangement of the upper magnetic field generator 2. As illustrated in FIG. 24, the upper magnetic field generator 2 is realized by an electromagnet. The electromagnet 2 applies a magnetic field according to a principle of electromagnetism. The electromagnet 2 can switch the application and shut-off of the magnetic field in accordance with the control by the magnetic field control circuitry 5. Specifically, the electromagnet 2 includes a core 22 around which a coil 21 is wound. The core 22 is a soft magnetic material having a columnar shape. A magnetic field is generated by the magnetic field control circuitry 5 passing an electric current through the coil 21, and the magnetic field is lost by the magnetic field control circuitry 5 shutting off the electric current.

Compared to the case of turning on the lower magnetic field generator 3 alone, when the upper magnetic field generator 2 and lower magnetic field generator 3 are turned on at the same time, the effect of the magnetic force, which is exerted on the magnetic particles 220 included in the sample 200, is as follows. When the magnetic pole of the surface 32a of the core 32, which is opposed to the cartridge 100, is different from the magnetic pole of a surface 22a of the core 22, which is opposed to the cartridge 100, that is, when these magnetic poles are opposed in SN arrangement or NS arrangement, the magnetic flux density in the sample 200 increases and the magnetic flux density gradient decreases by simultaneously turning on the upper magnetic field generator 2 and lower magnetic field generator 3. When these magnetic poles are identical, that is, when these magnetic poles are opposed in SS arrangement or NN arrangement, the magnetic flux density in the sample 200 decreases and the magnetic flux density gradient increases by simultaneously turning on the upper magnetic field generator 2 and lower magnetic field generator 3. The magnetic force acting on the magnetic particles 220 is proportional to the product between the magnetic flux density and magnetic flux density gradient at the position of each magnetic particle. Thus, by simultaneously turning on the lower magnetic field generator 3 and upper magnetic field generator 2 such that the opposed magnetic poles become identical or different, it becomes possible to make larger or smaller the magnetic force acting on the magnetic particles 220 than in the case of turning on the magnetic field by the lower magnetic field generator 3 alone. When the magnetic force acting on the magnetic particles 220 becomes larger, the magnetic particles 220 can be collected to the sensing area 120 more quickly than in the case of turning on the magnetic field by the lower magnetic field generator 3 alone, and the test time can be shortened. When there is no need to shorten the test time, the permanent magnet 31 can be replaced with a permanent magnet having an accordingly smaller surface magnetic flux density. As a result, it is possible to decrease the torque occurring in accordance with the ON/OFF switching of the lower magnetic field generator 3.

The lower magnetic field generator 3, which switches the ON/OFF of the magnetic field by utilizing the permanent magnet 31, is excellent in applying a strong magnetic field, but it is difficult to adjust the magnetic force. Thus, the magnetic field control circuitry 5 is configured to apply the composite magnetic field of the magnetic field generated from the lower magnetic field generator 3 and the magnetic field generated from the upper magnetic field generator 2, thereby to apply the magnetic field for attracting the magnetic particles 220 to the sensing area 120. By controlling the quantity of electricity (current value) of the electric current which is caused to flow in the electromagnet 2, the magnetic field control circuitry 5 adjusts the magnetic force of the composite magnetic field for attracting the magnetic particles 220 to the sensing area 120.

This magnetic force varying mechanism can be utilized when a plurality of different detection target substances are to be detected. Specifically, when a length of time is needed for a specific reaction of the detection target substance with a first substance which is fixed to the magnetic particle 220, the magnetic field control circuitry 5 weakens the magnetic force and keeps for a long time the state in which the magnetic particles 220 are dispersed in the sample 200, thereby enhancing the reaction rate between the detection target substance and the first substance. In addition, when a specific reaction of a detection target molecule 411 with a first substance 421 which is fixed to the magnetic particle 220 is completed relatively quickly, the magnetic field control circuitry 5 increases the magnetic force and quickly collects the magnetic particles 220 to the sensing area 120, thereby shortening the test time. Thereby, the magnetic force can be properly set in accordance with the characteristics of the detection target molecule, the detection reagent such as magnetic particles to be reacted with the detection target molecule, etc., and the sample analysis can be efficiently carried out.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A sample analyzer comprising:
   a detector configured to detect a target substance bonded to a magnetic particle which is included in a sample in a cartridge and collected to a sensing area in the cartridge;
   a first magnetic field generator which is an apparatus configured to apply a first magnetic field to the sample for moving the magnetic particles included in the sample from the sensing area, the first magnetic field generator being configured to switch application and shut-off of the first magnetic field; and a second magnetic field generator including a movable first permanent magnet configured to generate a second magnetic field for attracting the magnetic particles included in the sample to the sensing area, a first soft magnetic material configured to be excited by the second magnetic field of first permanent magnet and apply a third magnetic field to the sample, and a second soft magnetic material configured to short-circuit a magnetic flux from the first permanent magnet, the second magnetic field generator being configured to switch application and shut-off of the second magnetic field by moving the first permanent magnet relative to the first soft magnetic material and the second soft magnetic material, wherein the first soft magnetic material has a columnar shape and has a substantially flat surface on a side facing the sensing area, and wherein the substantially flat surface is substantially equal in size to the sensing area.

2. The sample analyzer of claim 1, wherein the first permanent magnet has a columnar shape and is provided to be rotatable about a rotational axis which is perpendicular to a longitudinal axis of the first permanent magnet, the first soft magnetic material has a columnar shape, and is disposed such that a longitudinal axis of the first soft magnetic material is parallel to the longitudinal axis of the first permanent magnet when a magnetic pole of the first permanent magnet has approached the first soft magnetic material, and the second soft magnetic material has a substantially C shape or a substantially U shape, and is disposed such that a center axis thereof is substantially aligned with the rotational axis.

3. The sample analyzer of claim 2, wherein the first permanent magnet, when applying the second magnetic field, rotates about the rotational axis such that one of the magnetic poles of the first permanent magnet approaches the first soft magnetic material, and the first permanent magnet, when shutting off the second magnetic field, rotates about the rotational axis such that both of the magnetic poles of the first permanent magnet approach the second soft magnetic material.

4. The sample analyzer of claim 2, further comprising:
a first torque reducing circuit configured to generate a torque for canceling a torque which occurs in accordance with the switching of the application and the shut-off of the second magnetic field by the first permanent magnet; and
a second torque reducing circuit configured to generate a torque for canceling the torque which occurs in accordance with the switching of the application and the shut-off of the second magnetic field by the first permanent magnet,
wherein the first torque reducing circuit and the second torque reducing circuit are disposed to be opposed to each other, with the second magnetic field generator being interposed,
wherein each of the first torque reducing circuit and the second torque reducing circuit includes:
a second permanent magnet having a columnar shape, coupled to the first permanent magnet via a coupling arm formed of a nonmagnetic material, and provided to be rotatable about the rotational axis together with the first permanent magnet; and a third soft magnetic material which is a soft magnetic material having an annular shape and disposed in a manner to surround the second permanent magnet, the third soft magnetic material having an inside diameter varying in accordance with an angle about the rotational axis, such that a distance between the third soft magnetic material and a magnetic pole of the second permanent magnet varies in accordance with rotation of the second permanent magnet about the rotational axis.

5. The sample analyzer of claim 4, wherein the first torque reducing circuit and the second torque reducing circuit have the same shape.

6. The sample analyzer of claim 4, wherein the second magnetic field generator, the first torque reducing circuit, and the second torque reducing circuit has a left-and-right symmetric geometry in a plane crossing a center of the second magnetic field generator and being perpendicular to the rotational axis.

7. The sample analyzer of claim 4, wherein an inner surface of the second soft magnetic material, which is opposed to the first permanent magnet, has a substantially arcuate shape formed such that a distance between the magnetic pole of the first permanent magnet and a part of the second soft magnetic material, which is opposed to the magnetic pole, becomes substantially constant regardless of rotation of the first permanent magnet about the rotational axis.

8. The sample analyzer of claim 4, wherein the second soft magnetic material of the second magnetic field generator is magnetically connected to at least one of the third soft magnetic material of the first torque reducing circuit and the third soft magnetic material of the second torque reducing circuit.

9. The sample analyzer of claim 1, further comprising a torque reducing circuit configured to generate a torque for canceling a torque which occurs in accordance with the switching of the application and the shut-off of the second magnetic field,
wherein the torque reducing circuit includes:
a second permanent magnet having a columnar shape, coupled to the first permanent magnet via a coupling arm formed of a nonmagnetic material, and provided to be rotatable about the rotational axis together with the first permanent magnet; and
a third soft magnetic material which is a soft magnetic material having an annular shape and disposed in a manner to surround the second permanent magnet, the third soft magnetic material having an inside diameter varying in accordance with an angle about the rotational axis, such that a distance between the third soft magnetic material and a magnetic pole of the second permanent magnet varies in accordance with rotation of the second permanent magnet about the rotational axis.

10. The sample analyzer of claim 1, further comprising control circuitry configured to control the first magnetic field generator and the second magnetic field generator in order to apply both the first magnetic field and the second magnetic field to the sample.

11. The sample analyzer of claim 10, wherein the first magnetic field generator includes an electromagnet, and
the control circuitry is configured to adjust a magnetic force of the composite magnetic field by controlling an electric current which is caused to flow in the electromagnet.

12. The sample analyzer of claim 1, wherein a substance, which specifically bonds to the target substance, is fixed to the sensing area.

13. The sample analyzer of claim 1, wherein the cartridge includes:
a container configured to store the sample;
the sensing area which is provided on a bottom surface of the container, and to which a substance that specifically bonds to the target substance is fixed; and
a light guide provided in contact with the sensing area, and configured to propagate light rays generated from a light source of the detector.

14. The sample analyzer of claim 1, further comprising control circuitry configured to apply, during a first predetermined time, the second magnetic field to the sample by the second magnetic field generator in order to attract the magnetic particles to the sensing area, to shut off, during a second predetermined time, both the first magnetic field of the first magnetic field generator and the second magnetic field of the second magnetic field generator, and to apply, during a third predetermined time, the first magnetic field to the sample by the first magnetic field generator in order to release the magnetic particles from the sensing area.

15. The sample analyzer of claim 1, wherein the first permanent magnet is provided to be slidable in a manner to approach, or move away from, the first soft magnetic material and the second soft magnetic material.

16. The sample analyzer of claim 15, wherein the first permanent magnet, when applying the second magnetic field, slides such that a magnetic pole of the first permanent magnet approaches the first soft magnetic material, and the first permanent magnet, when shutting off the second magnetic field, slides such that the magnetic poles of the first permanent magnet approach the second soft magnetic material.

17. The sample analyzer of claim 16, further comprising a torque reducing circuit configured to generate a torque for canceling a torque which occurs in accordance with the switching of the application and the shut-off of the second magnetic field by the first permanent magnet,
wherein the torque reducing circuit includes:
a second permanent magnet having a columnar shape, coupled to the first permanent magnet via a coupling arm formed of a nonmagnetic material, and provided to be rotatable about the rotational axis together with the first permanent magnet; and
a third soft magnetic material which is a soft magnetic material having an annular shape and disposed in a manner to surround the second permanent magnet, the third soft magnetic material having an inside diameter varying in accordance with an angle about the rotational axis, such that a distance between the third soft magnetic material and a magnetic pole of the second permanent magnet varies in accordance with rotation of the second permanent magnet about the rotational axis.

18. The sample analyzer of claim 16, further comprising a torque reducing circuit configured to generate a torque for canceling a torque which occurs in accordance with the switching of the application and the shut-off of the second magnetic field by the first permanent magnet,
wherein the torque reducing circuit includes:
a second permanent magnet having a columnar shape, coupled to the first permanent magnet via a coupling portion formed of a nonmagnetic material, and provided to be slidable together with the first permanent magnet; and
a third soft magnetic material which is a soft magnetic material having a substantially C shape, a substantially U shape or an annular shape and disposed such that a center axis thereof substantially matches with a longitudinal axis of the second permanent magnet, the third soft magnetic material having an inside diameter varying with respect to a slide direction of the second permanent magnet, such that a distance between the third soft magnetic material and a magnetic pole of the second permanent magnet varies in accordance with sliding of the second permanent magnet.

* * * * *

UNITED STATES PATENT AND TRADEMARK OFFICE
CERTIFICATE OF CORRECTION

Page 1 of 1

PATENT NO. : 10,317,399 B2
APPLICATION NO. : 15/293806
DATED : June 11, 2019
INVENTOR(S) : Naru Ikeda et al.

It is certified that error appears in the above-identified patent and that said Letters Patent is hereby corrected as shown below:

On the Title Page

Item (30) under Foreign Application Priority Data, the Japanese Priority Application No. "2015-206591" should be --2015-203591--.

Signed and Sealed this
Fourteenth Day of April, 2020

Andrei Iancu
*Director of the United States Patent and Trademark Office*